US012758651B2

(12) United States Patent
Christie et al.

(10) Patent No.: US 12,758,651 B2
(45) Date of Patent: Oct. 13, 2026

(54) COMPOSITIONS AND METHODS FOR DELIVERING PHARMACEUTICALLY ACTIVE AGENTS

(71) Applicant: MEDIMMUNE, LLC, Gaithersburg, MD (US)

(72) Inventors: Ronald James Christie, Gaithersburg, MD (US); Morgan Audrey Urello, Gaithersburg, MD (US)

(73) Assignee: MEDIMMUNE, LLC

( * ) Notice: Subject to any disclaimer, the term of this patent is extended or adjusted under 35 U.S.C. 154(b) by 881 days.

(21) Appl. No.: 17/997,376

(22) PCT Filed: Apr. 28, 2021

(86) PCT No.: PCT/US2021/029528

§ 371 (c)(1),
(2) Date: Oct. 28, 2022

(87) PCT Pub. No.: WO2021/222336

PCT Pub. Date: Nov. 4, 2021

(65) Prior Publication Data

US 2023/0165974 A1 Jun. 1, 2023

Related U.S. Application Data

(60) Provisional application No. 63/017,281, filed on Apr. 29, 2020.

(51) Int. Cl.

| | |
|---|---|
| ***C07D 279/12*** | (2006.01) |
| ***A61K 47/64*** | (2017.01) |
| ***A61K 47/69*** | (2017.01) |
| ***A61K 48/00*** | (2006.01) |
| ***C07D 213/82*** | (2006.01) |
| ***C07D 295/15*** | (2006.01) |

(52) U.S. Cl.

CPC ...... *A61K 48/0041* (2013.01); *A61K 47/6455* (2017.08); *A61K 47/6935* (2017.08); *C07D 213/82* (2013.01); *C07D 279/12* (2013.01); *C07D 295/15* (2013.01)

(58) Field of Classification Search

CPC ............ A61K 48/0041; A61K 47/6455; A61K 47/6935; A61K 48/0025; A61K 9/5169; A61K 47/60; A61K 9/00; C07D 213/82; C07D 279/12; C07D 295/15; C07D 213/80; C07D 295/145; C07K 1/1077; C07K 14/001; C07K 14/0019; C08G 69/10; C12N 15/88

See application file for complete search history.

(56) References Cited

U.S. PATENT DOCUMENTS 5,164,372 A * 11/1992 Matsuo .................. A61P 17/00 514/17.7

OTHER PUBLICATIONS

HyperPhysics, "Chemical Bonds" available online on Aug. 23, 1999, retrieved from https://hyperphysics.phy-astr.gsu.edu/hbase/Chemical/bond.html on Dec. 17, 2025 (Year: 1999).*

Ball, P., "What is a Bond?" first available online on Jan. 29, 2014 at https://www.chemistryworld.com/features/what-is-a-bond/6983.article at pg. accessed on Dec. 17, 2025 (Year: 2014).*

Kacan et al., Spectrochimica Acta Part A: Molecular and Biomolecular Spectroscopy, vol. 118, 2014,pp. 572-577 (Year: 2014).*

PubChem Compound Summary for CID 67831919, (2S)-2-amino-6-(morpholine-4-carbonylamino)hexanoic acid. Created on Nov. 30, 2012. Retrieved Dec. 19, 2025 from https://pubchem.ncbi.nlm.nih.gov/compound/67831919, (Year: 2012).*

International Search Report for PCT/US2021/029528 dated Jun. 8, 2021.

PubChem CID, Compound Summary, 2S)-2-Amino-6-(morpholine-4-carbonylamino)hexanoic acid, pp. 1-12. Dated Jun. 28, 2021.

* cited by examiner

*Primary Examiner* — Lianko G Garyu
*Assistant Examiner* — Claudia Espinosa
(74) *Attorney, Agent, or Firm* — Global IP

(57) ABSTRACT

The invention relates to modified lysines of the formula (I). The invention further relates to polypeptides comprising one or more modified lysine residues, pharmaceutical delivery systems comprising these polypeptides, pharmaceutical compositions containing them, and to their use in therapy.

(I)

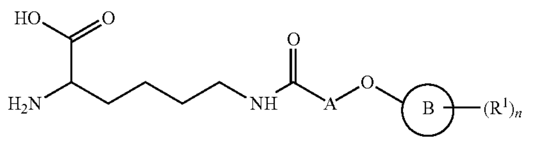

8 Claims, 5 Drawing Sheets

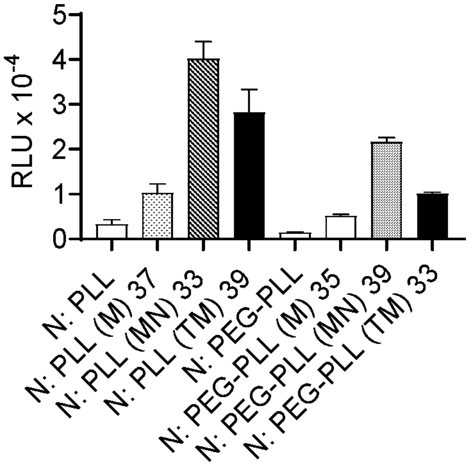
Figure 4A
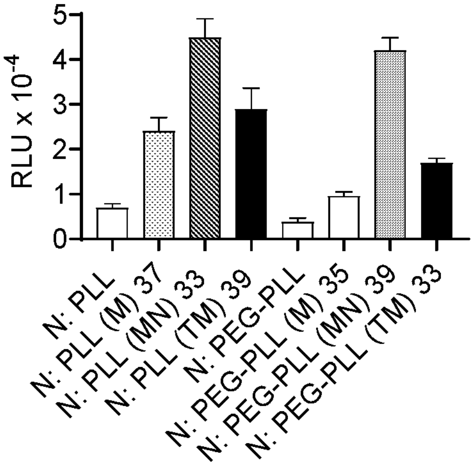
Figure 4B
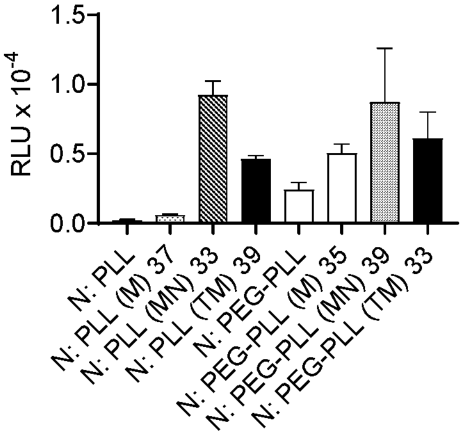
Figure 4C
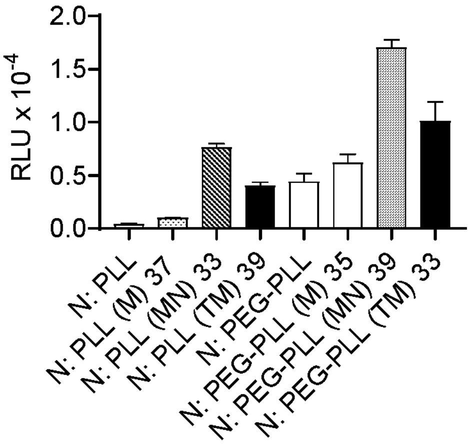
Figure 4D
Figure 4

COMPOSITIONS AND METHODS FOR DELIVERING PHARMACEUTICALLY ACTIVE AGENTS

RELATED APPLICATIONS

This application claims the benefit of priority under 35 USC 119(e) to U.S. Provisional Patent Application No. 63/017,281, filed Apr. 29, 2020, the entirety of which is incorporated herein by reference.

FIELD

The present specification relates to modified lysines, polypeptides comprising these modified lysines and the use of these polypeptides for delivering pharmaceutically active agents, particularly genetic material, into a cell. The present specification further relates to the use of these polypeptides in therapy.

BACKGROUND

Gene therapy is the medical field that focuses on the therapeutic delivery of (foreign) genetic material (such and DNA and RNA) into a patient's cells in order to treat a disease. To date, several gene therapies including Luxturna® (RPE65 mutation-induced blindness) and Kymriah® (chimeric antigen receptor T cell therapy) have received regulatory approval for a number of different medical conditions.

Gene delivery is the process used to introduce the genetic material into a cell. To be successful, the genetic material must remain stable during transport and ultimately be internalized into the targeted cell. When the genetic material is DNA, it must be internalized into the targeted cell and delivered into the nucleus. Gene delivery requires a vector, and suitable vectors generally fall into two categories—viral, and non-viral, vectors.

Virus mediated gene delivery utilizes the ability of a virus to inject its DNA inside a host cell. The genetic material is packaged into a replication-deficient viral particle in order to form a viral vector. Viral methods are highly efficient but can induce an immune response. Furthermore, they can only deliver very small pieces of genetic material into the cells, producing them is labour-intensive, and there are risks of random insertion sites, cytopathic effects and mutagenesis.

Synthetic vectors offer several advantages over viruses for gene delivery applications in regard to structural versatility and scalability; and they may be designed solely and specifically to achieve one desired purpose. These materials can be designed to package the genetic material into nanoparticles or vesicles which have been engineered to overcome biological barriers associated with cell uptake, transport into the cytosol, and (if desired) delivery into the nucleus. A common approach is to package the genetic material into multimolecular assemblies with materials such as polymers, peptides, or lipids comprising positive charges which associate with the anionic nucleic acids. Electrostatic interactions between the positive and negative charges drive self-assembly into nano- or microparticle structures, and the size and shape of these particles can be controlled by material type and condensation conditions (Park et al. Adv Drug Del Rev, 2006, 58(4):467-86).

Formulation of DNA, for example, into a suitable vector like a nanoparticle significantly improves cellular uptake of DNA when compared to uptake of unformulated DNA. DNA has a net negative charge and is not typically internalized into cells (which also have a net negative charge) on its own. Unformulated DNA also tends to trigger an immune response which leads to its degradation. Formulation of the DNA into a suitable vector can neutralise its negative charge and protect it from degradation in the extracellular space.

In order for the vector to be effectively internalised, it must be transported into the cell via a process called endocytosis. During this process, the vector is surrounded by an area of cell membrane, which then buds off inside the cell to form an endosome. The vector must be designed to allow this process to occur, but then mitigate the possibility of lysosome entrapment, i.e. sequestration into the acidic membrane-bound lysosome compartments. One way of achieving this is to ensure the endosome ruptures before lysosomal trafficking can occur. This may be achieved by the vector buffering the endosome pH (the endosome becomes increasingly acidic after cell uptake) until the resulting osmotic gradient causes the endosome to burst and release the genetic material into the cytoplasm where it can be available for transcription/translation. Suitable vector materials with efficient buffering capacity over the endosomal buffering range (pH 7.4-pH 5.0) can slow the acidification of the endosome by accepting protons, which causes an influx of further protons and counter ions from the cytosol.

Current synthetic gene delivery systems are limited in vivo by low stability, high toxicity, and inefficient cytoplasmic entry of the genetic material. Engineering a multifunctional material suitable for gene delivery that achieves an optimal balance between formulation properties (size, charge, etc.), stability, buffering capacity, and toxicity, whilst maintaining a high delivery efficiency has proved difficult and complex, but would significantly simplify the resulting formulation.

Polylysine (PL) is a linear polypeptide bearing free amine side arms that are able to interact with negatively charged nucleic acids and form complexes via electrostatic interaction. For this reason, PL and its copolymers have been used extensively in the laboratory as vectors in non-viral gene delivery. For instance, PL-based DNA nanoparticles have demonstrated high efficiency transfection in multiple cell lines when coupled with transfection aids such as chloroquine (Yamauchi et al. Biomaterials, 2003 24(24): 4495-4506). and as a vital component of block copolymers or hybrid systems (Incani et al. ACS Appl. Mater. Interfaces, 2009, 1(4): 841-848). PL is also biodegradable which is advantageous for in vivo applications. However, PL transfection efficiency is much lower than other cationic polymeric transfection agents (for example polyethylenimine (PEI)) despite facilitating similar cellular uptake levels of DNA. This inefficient transfection has been linked to the inability of the resulting DNA nanoparticles to escape the endosome potentially due to their inability to buffer the endosomal pH (Hwang et al. Biomacro., 2014, 15(10):2577-86).

The incorporation of protonatable groups with pKa $<6.5$ such as imidazoles or histidines has been shown to enhance PL nanoparticle transfection (Roufai et al. Bioconjug. Chem., 2001 12(1): 92-99, and Hwang et al. Biomacro., 2014, 15(10):2577-86); however, in order to ensure nanoparticle stability at a neutral pH a vital balance must be struck between protonatable groups with pKa above and below 7.4. For instance, previous studies (Benns et al. Bioconjug. Chem., 2000, 11(5):637-45) have investigated the amino acid histidine (pKa=6) as a functional group to improve PL buffering. Histidine grafted onto polylysine was shown to boost buffering capacity up to 3.5-fold relative to PL. Benns also grafted polyhistidine onto other polymers and reported even greater enhancements in buffering (~4.5-fold (Hwang et al. Biomacro., 2014, 15(10):2577-86) along with dramatic improvements in transfection.

The present application describes certain modified lysines that can be used to form modified PLs with increased delivery efficiency of genetic material when compared to unmodified PLs. These modified PLs are unique in that they are multifunctional unlike the histidine modifications which only facilitate endosomal buffering. These modified PLs: i) possess enhanced buffering properties tuned to enable protonation during the pH transition that occurs during cellular internalization and lysosomal trafficking, ii) are more stable due to increased nucleic acid binding through electrostatic and non-electrostatic (e.g. pi-pi stacking) interactions and/or iii) have increased biocompatibility when metabolite-based core units are used which are naturally occurring and less likely to be toxic or immunogenic. These modified PLs form nanoparticles with plasmid DNAs, similar to those formed with unmodified PL (~100 nm, spheres, rods, and toroids) and demonstrate higher serum stability and prolonged blood circulation following intravenous injection in mice without associated toxicity. They protect the encapsulated genetic material by not disassociating easily and stay in circulation longer. The modified lysines described herein are multifunctional units that can be incorporated into vectors and improve transfection of synthetic gene delivery systems whilst maintaining high biocompatibility.

SUMMARY

This specification describes, in part, a modified lysine of formula (I):

(I)

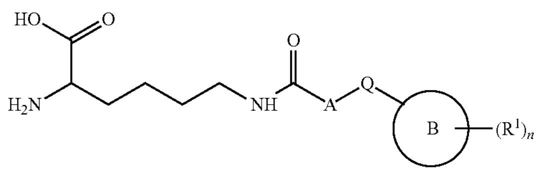

wherein:

A is a bond, $C_{1-6}$alkylene, carbocyclyl or heterocyclyl; wherein said carbocyclyl or heterocyclyl may be optionally substituted on carbon by one or more $R^2$; and wherein if said heterocyclyl contains an —NH— moiety that nitrogen may be optionally substituted by a group selected from RA;

Q is a bond, carbocyclyl or heterocyclyl; wherein said carbocyclyl or heterocyclyl may be optionally substituted on carbon by one or more $R^3$; and wherein if said heterocyclyl contains an —NH-moiety that nitrogen may be optionally substituted by a group selected from $R^B$;

Ring B is morpholinyl or thiomorpholinyl; wherein if said morpholinyl or thiomorpholinyl contains an —NH— moiety that nitrogen may be optionally substituted by a group selected from $R^C$;

$R^1$, $R^2$ and $R^3$ are each independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl and N-methyl-N-ethylsulphamoyl;

n is 0-4;

$R^A$, $R^B$ are $R^C$ are independently selected from methyl, ethyl, propyl, isopropyl, acetyl, mesyl, ethylsulphonyl, methoxycarbonyl, ethoxycarbonyl, propoxycarbonyl, butoxycarbonyl, carbamoyl, N-methylcarbamoyl, N-ethylcarbamoyl, N,N-dimethylcarbamoyl, N,N-diethykarbamoyl and N-methyl-N-ethylcarbamoyl.

This specification also describes, in part, a polypeptide comprising one or more modified lysine residues as described herein.

This specification also describes, in part, a polypeptide as described herein for use as a pharmaceutical delivery system.

This specification also describes, in part, a pharmaceutical composition which comprises a polypeptide as described herein and a pharmaceutically active agent.

This specification also describes, in part, a method of therapy in a warm-blooded animal, such as man, which comprises administering to said animal an effective amount of a pharmaceutical composition as described herein.

DETAILED DESCRIPTION OF THE INVENTION

Many embodiments of the invention are detailed throughout the specification and will be apparent to a reader skilled in the art. The invention is not to be interpreted as being limited to any of the recited embodiments.

"A" means "at least one". In any embodiment where "a" is used to denote a given material or element, "a" may mean one.

"Comprising" means that a given material or element may contain other materials or elements. In any embodiment where "comprising" is mentioned the given material or element may be formed of at least 10% w/w, at least 20% w/w, at least 30% w/w, or at least 40% w/w of the material or element. In any embodiment where "comprising" is mentioned, "comprising" may also mean "consisting of" (or "consists of") or "consisting essentially of" (or "consists essentially of") a given material or element.

"Consisting of" or "consists of" means that a given material or element is formed entirely of the material or element. In any embodiment where "consisting of" or "consists of" is mentioned the given material or element may be formed of 100% w/w of the material or element.

"Consisting essentially of" or "consists essentially of" means that a given material or element consists almost entirely of that material or element. In any embodiment where "consisting essentially of" or "consists essentially of" is mentioned the given material or element may be formed of at least 50% w/w, at least 60% w/w, at least 70% w/w, at least 80% w/w, at least 90% w/w, at least 95% w/w or at least 99% w/w of the material or element.

In any embodiment where "is" or "may be" is used to define a material or element, "is" or "may be" may mean the material or element "consists of" or "consists essentially of" the material or element.

In any embodiment of this specification where "about" is mentioned, "about" may mean+/−0 (i.e. no variance), +/−0.01, +/−0.05, +/−0.1, +/−0.5, +/−1, +/−2, +/−5, +/−10 or +/−20 percent of the figure quoted. Where a figure is quoted, in a further embodiment this further refers to about the figure quoted.

Claims are embodiments.

Disclosed herein is a modified lysine of formula (I):

(I)

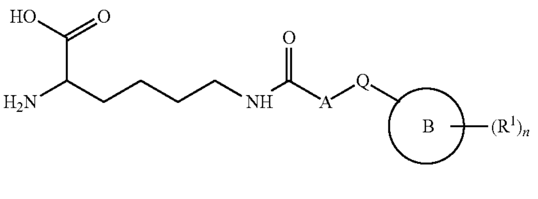

wherein A, Q, B, $R^2$ and n are as herein described.

In one embodiment A is a bond.

In one embodiment A is $C_{1-6}$alkylene.

In one embodiment A is methylene.

In one embodiment A is carbocyclyl; wherein said carbocyclyl may be optionally substituted on carbon by one or more $R^2$.

In one embodiment A is heterocyclyl; wherein said heterocyclyl may be optionally substituted on carbon by one or more $R^2$; and wherein if said heterocyclyl contains an —NH— moiety that nitrogen may be optionally substituted by a group selected from $R^A$.

In one embodiment A is heterocyclyl.

In one embodiment A is a pyridyl.

In one embodiment A is a bond, $C_{1-6}$alkylene or heterocyclyl.

In one embodiment A is a bond, methylene or a pyridyl.

In one embodiment Q is a bond.

In one embodiment Q is carbocyclyl; wherein said carbocyclyl may be optionally substituted on carbon by one or more $R^3$.

In one embodiment Q is heterocyclyl; wherein said heterocyclyl may be optionally substituted on carbon by one or more $R^3$; and wherein if said heterocyclyl contains an —NH— moiety that nitrogen may be optionally substituted by a group selected from $R^B$.

In one embodiment Ring B is morpholinyl.

In one embodiment Ring B is morpholinyl; wherein if said morpholinyl contains an —NH— moiety that nitrogen may be optionally substituted by a group selected from $R^C$.

In one embodiment Ring B is thiomorpholinyl.

In one embodiment Ring B is thiomorpholinyl; wherein if said thiomorpholinyl contains an —NH-moiety that nitrogen may be optionally substituted by a group selected from $R^C$.

In one embodiment $R^1$ is halo.

In one embodiment n is 0.

In one embodiment n is 1.

In one embodiment n is 2.

In one embodiment n is 3.

In one embodiment n is 4.

In one embodiment there is provided a modified lysine of formula (I) wherein

A is a bond, $C_{1-6}$alkylene or heterocyclyl;

Q is a bond;

Ring B is morpholinyl or thiomorpholinyl; and n is 0.

In one embodiment there is provided a modified lysine of formula (I) wherein

A is a bond, methylene or a pyridyl;

Q is a bond;

Ring B is morpholinyl or thiomorpholinyl; and n is 0.

In one aspect of the invention the modified lysine of formula (I) is a modified lysine of formula (IA):

(IA)

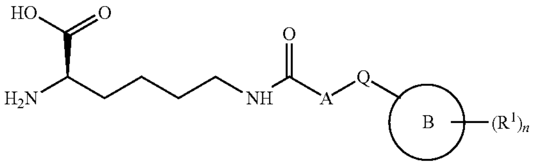

wherein A, Q, B, $R^1$ and n are as herein described. A modified lysine of formula (IA) may also be referred to as a modified D-lysine.

In one aspect of the invention the modified lysine of formula (I) is a modified lysine of formula (IB):

(IB)

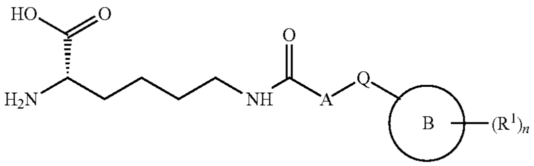

wherein A, Q, B, $R^1$ and n are as herein described. A modified lysine of formula (IB) may also be referred to as a modified L-lysine.

In one aspect of the invention the modified lysine of formula (I) is selected from:

2-amino-6-{[6-(morpholin-4-yl)pyridine-3-carbonyl]amino}hexanoic acid;

2-amino-6-[(thiomorpholine-3-carbonyl)amino]hexanoic acid; and 2-amino-6-[2-(morpholin-4-yl)acetamido]hexanoic acid.

In one aspect of the invention the modified lysine of formula (I) is selected from:

(R)-2-amino-6-{[6-(morpholin-4-yl)pyridine-3-carbonyl]amino}hexanoic acid;

(R)-2-amino-6-[(thiomorpholine-3-carbonyl)amino]hexanoic acid; and (R)-2-amino-6-[2-(morpholin-4-yl)acetamido]hexanoic acid.

In one aspect of the invention the modified lysine of formula (I) is selected from:

(S)-2-amino-6-{[6-(morpholin-4-yl)pyridine-3-carbonyl]amino}hexanoic acid;

(S)-2-amino-6-[(thiomorpholine-3-carbonyl)amino]hexanoic acid; and (S)-2-amino-6-[2-(morpholin-4-yl)acetamido]hexanoic acid.

In one aspect of the invention the modified lysine of formula (I) is selected from:

2-amino-6-{[6-(morpholin-4-yl)pyridine-3-carbonyl]amino}hexanoic acid;

2-amino-6-[(thiomorpholine-3-carbonyl)amino]hexanoic acid; and 2-amino-6-[2-(morpholin-4-yl)acetamido]hexanoic acid, in salt form.

In one aspect of the invention the modified lysine of formula (I) is selected from:

(R)-2-amino-6-{[6-(morpholin-4-yl)pyridine-3-carbonyl]amino}hexanoic acid;

(R)-2-amino-6-[(thiomorpholine-3-carbonyl)amino]hexanoic acid; and (R)-2-amino-6-[2-(morpholin-4-yl)acetamido]hexanoic acid, in salt form.

In one aspect of the invention the modified lysine of formula (I) is selected from:

(S)-2-amino-6-{[6-(morpholin-4-yl)pyridine-3-carbonyl]amino}hexanoic acid;

(S)-2-amino-6-[(thiomorpholine-3-carbonyl)amino]hexanoic acid; and (S)-2-amino-6-[2-(morpholin-4-yl)acetamido]hexanoic acid, in salt form.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to a parent group. As used herein, the term "optionally substituted" means that the chemical group may have no substituents (i.e. unsubstituted) or may have one or more substituents (i.e. substituted). It is to be understood that substitution at a given atom is limited by valency. Where optional substituents are selected from a list of groups it is to be understood that this definition includes all substituents being chosen from one of the specified groups or the substituents being chosen from two or more of the specified groups. Where there may be more than one of the same substituent, e.g. $R^2$, it is to be understood that this definition also includes all such substituents being chosen from one of the specified groups or the substituents being chosen from two or more of the specified groups.

As used herein, the term "Cu" indicates a range of the carbon atoms numbers, wherein i and j are integers and the range of the carbon atoms numbers includes the endpoints (i.e. i and j) and each integer point in between, and wherein j is greater than i. For examples, $C_{1-6}$ indicates a range of one to six carbon atoms, including one carbon atom, two carbon atoms, three carbon atoms, four carbon atoms, five carbon atoms and six carbon atoms. In some embodiments, the term "$C_{3-6}$" indicates 1 to 6, 1 to 5, 1 to 4, 1 to 3 or 1 to 2 carbon atoms.

As used herein, the term "alkyl", whether as part of another term or used independently, refers to a saturated hydrocarbon chain. The hydrocarbon chain mentioned above may be straight-chain or branched-chain. The term "$C_{i-j}$alkyl" refers to an alkyl having i to j carbon atoms. Examples of $C_{1-6}$alkyl include, but are not limited to, methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. References to groups such as "butyl" without further qualification refer to all forms of butyl, for example n-butyl and tert-butyl etc.

As used herein, the term "alkylene", whether as part of another term or used independently, refers to a saturated hydrocarbon chain. The hydrocarbon chain mentioned above may be straight-chain or branched-chain. The term "C alkylene" refers to an alkyl having i to j carbon atoms. Examples of $C_{3-6}$alkylene include, but are not limited to, methylene ($—CH_2—$), ethylene ($—CH_2—CH_2—$), propylene ($—CH_2—CH_2—CH_2—$) and butylene ($—CH_2—CH_2—CH_2—CH_2—$ and $—CH_2—CH(CH_3)—CH_2—$ etc) and the like.

As used herein the term "halo" refers to fluoro, chloro, bromo and iodo.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a $—CH_2—$ group can optionally be replaced by a —C(O)— and a ring sulphur atom may be optionally oxidised to form the 5-oxides. Examples and suitable values of the term "heterocyclyl" are morpholino, piperidyl, pyridyl, pyranyl, pyrrolyl, pyrazolyl, isothiazolyl, indolyl, quinolyl, thienyl,1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone and 4-thiazolidone. A particular example of the term "heterocyclyl" is pyridyl. In one aspect of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a $—CH_2—$ group can optionally be replaced by a —C(O)— and a ring sulphur atom may be optionally oxidised to form the S-oxides.

A "carbocyclyl" is a saturated, partially saturated or unsaturated, mono or bicyclic carbon ring in that contains 3-12 atoms; wherein a $—CH_2—$ group can optionally be replaced by a —C(O)—. In one embodiment "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. A particular example of "carbocyclyl" is phenyl.

The "compounds" of the present disclosure encompass all isotopes of atoms in the compounds. Isotopes of an atom include atoms having the same atomic number but different mass numbers. For example, unless otherwise specified, hydrogen, carbon, nitrogen, oxygen, phosphorous, sulphur, fluorine, chlorine, bromide or iodine in the "compound" of present disclosure are meant to also include their isotopes such as but are not limited to: $^{1}H$, $^{2}H$, $^{3}H$, $^{11}C$, $^{12}C$, $^{13}C$, $^{14}C$, $^{14}N$, $^{15}N$, $^{16}O$, $^{17}O$, $^{18}O$, $^{31}P$, $^{32}P$, $^{32}S$, $^{33}S$, $^{34}S$, $^{36}S$, $^{17}F$, $^{19}F$, $^{35}Cl$, $^{37}Cl$, $^{79}Br$, $^{81}Br$, $^{127}I$ and $^{131}I$. In some embodiments, hydrogen includes protium, deuterium and tritium. In some embodiments, hydrogen refers to protium. In some embodiments, hydrogen refers to deuterium. In some embodiments, hydrogen refers to tritium. In some embodiments, the term "substituted by deuterium" or "deuterium substituted" to replace the other isoform of hydrogen (e.g. protium) in the chemical group with deuterium. In some embodiments, carbon includes $^{12}C$ and $^{13}C$.

Residue

The amino acids in the polypeptides described herein are linked together to form a chain via peptide bonds between the α-amino group and the carboxy groups. Once linked in the chain, an individual amino acid is referred to as a "residue".

Modified Lysine

In any embodiment where modified lysines or modified lysine residues are mentioned, these refer to lysines modified according to formula (I) and embodiments thereof.

In any embodiment where a modified lysine or modified lysine residue is mentioned, this may refer to a modified D-lysine.

In any embodiment where a modified lysine or modified lysine residue is mentioned, this may refer to a modified L-lysine.

In any embodiment where a modified lysine or modified lysine residue is mentioned, this may refer to a modified lysine or modified lysine residue in salt form.

As used herein, "salt form" refers to derivatives of the modified lysine, modified lysine residue or polypeptides described herein wherein the parent compound is modified by converting one or more existing acidic moieties (e.g. carboxyl and the like) and/or base moieties (e.g. amine, alkali and the like) to its salt form. In many cases, compounds of present disclosure are capable of forming acid and/or base salts by virtue of the presence of amino and/or carboxyl groups or groups similar thereto. A particular salt form is a pharmaceutically acceptable salt. As used herein a "pharmaceutically acceptable salt" is a salt that is safe and effective for use in mammals, particularly human beings.

Suitable salt forms of a modified lysine, modified lysine residue or polypeptides described herein includes, for example, an acid-addition salt, which can be derived from for example an inorganic acid (for example, hydrochloric, hydrobromic, sulfuric, nitric, phosphoric acid and the like) or organic acid (for example, formic, acetic, propionic, glycolic, oxalic, maleic, malonic, succinic, fumaric, tartaric, trimesic, citric, lactic, phenylacetic, benzoic, mandelic, methanesulfonic, napadisylic, ethanesulfonic, toluenesulfonic, trifluoroacetic, salicylic, sulfosalicylic acids and the like). A particular acid-addition salt is a hydrochloride.

Suitable salt forms of a modified lysine, modified lysine residue or polypeptides described herein includes, for example, an base-addition salt, which can be derived from for example an inorganic bases (for example, sodium, potassium, ammonium salts and hydroxide, carbonate, bicarbonate salts of metals from columns I to XII of the periodic table such as calcium, magnesium, iron, silver, zinc, copper and the like) or organic bases (for example, primary, secondary, and tertiary amines, substituted amines including naturally occurring substituted amines, cyclic amines, basic ion exchange resins, and the like). Certain organic amines include but are not limited to isopropylamine, benzathine, cholinate, diethanolamine, diethylamine, lysine, meglumine, piperazine and tromethamine. Lists of additional suitable salts can be found, e.g. in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Polypeptide

In a further feature of the invention there is provided a polypeptide comprising one or more modified lysine residues as described herein. Herein where a polypeptide is mentioned, this refers to a chain of amino acid residues.

In any embodiment where a polypeptide is mentioned, this may refer to a polypeptide synthesised via techniques that allow precise control over its composition and purity. Suitable techniques include solid phase peptide synthesis.

In any embodiment where a polypeptide is mentioned, this may refer to a polypeptide synthesised via a polymerisation reaction. Suitable techniques include addition or condensation polymerization.

In any embodiment where a polypeptide is mentioned, this may refer to a continuous, and unbranched chain of amino acid residues.

In any embodiment where a polypeptide is mentioned, this may refer to a polypeptide comprising 2-1000 amino acid residues.

In any embodiment where a polypeptide is mentioned, this may refer to a polypeptide comprising 2-50 amino acid residues.

In any embodiment where a polypeptide is mentioned, this may refer to a polypeptide comprising 10-500 amino acid residues.

In any embodiment where a polypeptide is mentioned, this may refer to a polypeptide comprising 15-40 amino acid residues.

In any embodiment where a polypeptide is mentioned, this may refer to a polypeptide comprising 20-100 amino acid residues.

In any embodiment where a polypeptide is mentioned, this may refer to a polypeptide comprising 20-50 amino acid residues.

In any embodiment where a polypeptide is mentioned, this may refer to a polypeptide comprising 25-1000 amino acid residues.

In any embodiment where a polypeptide is mentioned, this may refer to a polypeptide comprising 25-500 amino acid residues.

In any embodiment where a polypeptide is mentioned, this may refer to a polypeptide comprising 25-100 amino acid residues.

In any embodiment where a polypeptide is mentioned, this may refer to a polypeptide comprising 25-40 amino acid residues.

In any embodiment where a polypeptide is mentioned, this may refer to a polypeptide comprising 30-40 amino acid residues.

In any embodiment where a polypeptide is mentioned, the polypeptide may be in salt form.

Polylysine

A polylysine is a polypeptide comprising two or more modified lysine residues, or a mix of lysine and modified lysine residues, wherein the peptide bonds in the chain are formed between the α-carboxyl and α-amino groups of lysine residues and/or modified lysine residues, and wherein all the amino acid residues are selected from modified lysine residues, or a mix of lysine and modified lysine residues.

In any embodiment where polylysine is mentioned, this may refer to a polylysine wherein all the modified lysine residues are the same.

In any embodiment where polylysine is mentioned, this may refer to a polylysine comprising two or more different modified lysine residues.

In any embodiment where polylysine is mentioned, this may refer to a poly-D-lysine.

In any embodiment where polylysine is mentioned, this may refer to a poly-L-lysine.

In any embodiment where polylysine is mentioned, this may refer to a racemic polylysine.

In any embodiment where polylysine is mentioned, this may refer to a poly-L/D-lysine.

In any embodiment where a polylysine is mentioned, this may refer to a polylysine comprising 2 1000 amino acid residues.

In any embodiment where a polylysine is mentioned, this may refer to a polylysine comprising 2 50 amino acid residues.

In any embodiment where a polylysine is mentioned, this may refer to a polylysine comprising 10-500 amino acid residues.

In any embodiment where a polylysine is mentioned, this may refer to a polylysine comprising 15-40 amino acid residues.

In any embodiment where a polylysine is mentioned, this may refer to a polylysine comprising 20-100 amino acid residues.

In any embodiment where a polylysine is mentioned, this may refer to a polylysine comprising 20-50 amino acid residues.

In any embodiment where a polylysine is mentioned, this may refer to a polylysine comprising 25-1000 amino acid residues.

In any embodiment where a polylysine is mentioned, this may refer to a polylysine comprising 25-500 amino acid residues.

In any embodiment where a polylysine is mentioned, this may refer to a polylysine comprising 25-100 amino acid residues.

In any embodiment where a polylysine is mentioned, this may refer to a polylysine comprising 25-40 amino acid residues.

In any embodiment where a polylysine is mentioned, this may refer to a polylysine comprising 30-40 amino acid residues.

In any embodiment where a polylysine is mentioned, the polylysine may be in salt form.

In any embodiment where a polylysine is mentioned, more than 10% of the lysine residues in the polylysine may be modified lysine residues.

In any embodiment where a polylysine is mentioned, more than 20% of the lysine residues in the polytysine may be modified lysine residues.

In any embodiment where a polylysine is mentioned, more than 30% of the lysine residues in the polytysine may be modified lysine residues.

In any embodiment where a polylysine is mentioned, more than 40% of the lysine residues in the polytysine may be modified lysine residues.

In any embodiment where a polylysine is mentioned, more than 50% of the lysine residues in the polytysine may be modified lysine residues.

In any embodiment where a polylysine is mentioned, more than 60% of the lysine residues in the polytysine may be modified lysine residues.

In any embodiment where a polylysine is mentioned, more than 70% of the lysine residues in the polytysine may be modified lysine residues.

In any embodiment where a polylysine is mentioned, more than 80% of the lysine residues in the polytysine may be modified lysine residues.

In any embodiment where a polylysine is mentioned, more than 90% of the lysine residues in the polytysine may be modified lysine residues.

In any embodiment where a polylysine is mentioned, fewer than 10% of the lysine residues in the polytysine may be modified lysine residues.

In any embodiment where a polylysine is mentioned, fewer than 20% of the lysine residues in the polytysine may be modified lysine residues.

In any embodiment where a polylysine is mentioned, fewer than 30% of the lysine residues in the polytysine may be modified lysine residues.

In any embodiment where a polylysine is mentioned, fewer than 40% of the lysine residues in the polytysine may be modified lysine residues.

In any embodiment where a polylysine is mentioned, fewer than 50% of the lysine residues in the polytysine may be modified lysine residues.

In any embodiment where a polylysine is mentioned, fewer than 60% of the lysine residues in the polytysine may be modified lysine residues.

In any embodiment where a polylysine is mentioned, fewer than 70% of the lysine residues in the polytysine may be modified lysine residues.

In any embodiment where a polylysine is mentioned, fewer than 80% of the lysine residues in the polytysine may be modified lysine residues.

In any embodiment where a polylysine is mentioned, fewer than 90% of the lysine residues in the polytysine may be modified lysine residues.

In any embodiment where a polylysine is mentioned, 10%-90% of the lysine residues in the polylysine may be modified lysine residues.

In any embodiment where a polylysine is mentioned, 10%-80% of the lysine residues in the polylysine may be modified lysine residues.

In any embodiment where a polylysine is mentioned, 10%-70% of the lysine residues in the polylysine may be modified lysine residues.

In any embodiment where a polylysine is mentioned, 20%-60% of the lysine residues in the polylysine may be modified lysine residues.

In any embodiment where a polylysine is mentioned, 25%-50% of the lysine residues in the polylysine may be modified lysine residues.

In any embodiment where a polylysine is mentioned, 25%-40% of the lysine residues in the polylysine may be modified lysine residues.

A terminal amino group may optionally be a modified amino group

In one embodiment, the terminal amino group of a polypeptide may be unmodified. An unmodified terminal amino group means it is an —$NH_2$ group.

In one embodiment, the terminal amino group of a polypeptide may be a modified amino group.

Modifications are typically chemical modifications which include, but are not limited to, adding chemical groups, creating new bonds, and removing chemical groups. Modified amino groups are well known to those skilled in the art and include, but are not limited to, acetylation, desamino, N-lower alkyl, N-di lower alkyl, constrained alkyl (e.g., branched, cyclic, fused, adamantyl) and N-acyl modifications. Modified amino groups may also include, but are not limited to, internal amide bond involving the N-terminus (e.g. pyroGlu) protected amino groups or attaching a radiolabel, fluorescent tag or affinity tag (e.g. biotin), or cell-targeting ligand.

Cell-targeting ligands refer to targeting moiety that binds to a cell and/or facilitates cellular internalization. Cell-targeting ligands may include but are not limited to polypeptide-based materials, such as cyclic RGD, transferrin receptor binding peptides, antibodies, or cell penetrating peptides, sugars, or small molecules like folate.

A suitable protecting group for an amino group is, for example, an acyl group, for example an alkanoyl group such as acetyl, an alkoxycarbonyl group, for example a methoxycarbonyl, ethoxycarbonyl ao or t-butoxycarbonyl group, an arylmethoxycarbonyl group, for example benzyloxycarbonyl, or an aroyl group, for example benzoyl. A particular modified amino group is acylamino. A particular modified amino group is acetylamino.

Lower alkyl is $C_{1-4}$alkyl, including t-butyl, butyl, propyl, isopropyl, ethyl and methyl.

In one embodiment, the terminal amino group of a polypeptide may be modified by the addition of a further polymer, optionally via a linking group.

In one embodiment, the terminal amino group of a polypeptide may be modified by the addition of a polyethylene glycol polymer, optionally via a linking group, to form a polyethylene glycol polylysine.

A Terminal Carboxy Group May Optionally be a Modified Carboxy Group

In one embodiment the terminal carboxy group of a polypeptide is unmodified. An unmodified terminal carboxy group means it is a —C(O)OH group.

In one embodiment one terminal carboxy group of a polypeptide is a modified carboxy group.

Modifications are typically chemical modifications which include, but are not limited to, adding chemical groups, creating new bonds, and removing chemical groups. Modified carboxy group are well known to those skilled in the art and include, but are not limited to, amide, lower alkyl amide, constrained alkyl (e.g., branched, cyclic, fused, adamantyl), dialkyl amide, and lower alkyl ester modifications. Modified carboxy groups many also include, but are not limited to, protected carboxy groups or attaching a radiolabel, fluorescent tag or affinity tag (e.g. biotin), or cell-targeting ligand. A suitable protecting group for a carboxy group is, for example, an esterifying group, for example a methyl ethyl group, t-butyl group, or a benzyl group. A particular modified carboxy group is —$CO_2NH_2$. A particular modified carboxy group is C-terminal amidation. A particular modified carboxy group is a carboxamide group. A particular modified carboxy group is N—($C_{1-4}$alkyl)carbamoyl group.

In one embodiment, the terminal carboxy group of a polypeptide may be modified by the addition of a further polymer, optionally via a linking group.

In one embodiment, the terminal carboxy group of a polypeptide may be modified by the addition of a polyethylene glycol polymer, optionally via a linking group, to form a polyethylene glycol polylysine.

Polyethylene Glycol Polylysine

Polyethylene glycol (PEG) is a polymer consisting of —$(OCH_2CH_2)_n$— repeating subunits where n>3. It is typically synthesised using ring-opening polymerization of ethylene oxide.

In any embodiment where polyethylene glycol polylysine is mentioned this refers to a polypeptide comprising both a polyethylene glycol polymer and a polylysine polypeptide.

In any embodiment where polyethylene glycol polylysine is mentioned this may be a polyethylene glycol polylysine comprising a substructure of the formula (IC):

(IC)

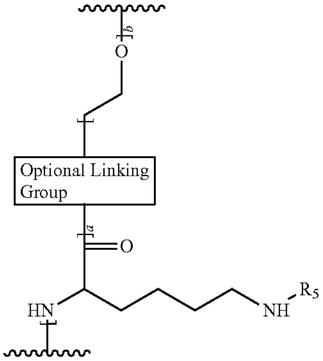

-continued $R_5$ is H or

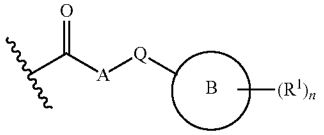

a and b indicate repeating units indicates a point of attachment to another atom or group A particular polyethylene glycol polylysine of formula (IC) is for example

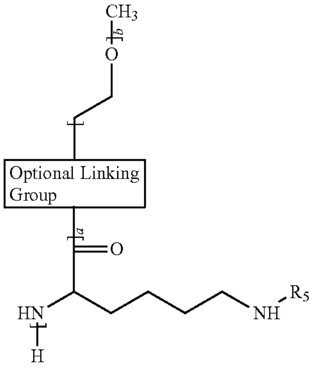

$R_5$ is H or

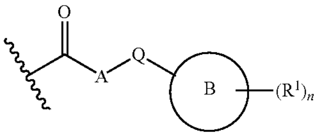

a and b indicate repeating units indicates a point of attachment to another atom or group In any embodiment where polyethylene glycol polylysine is mentioned this may be a polyethylene glycol polylysine comprising a substructure of the formula (ID):

(ID)

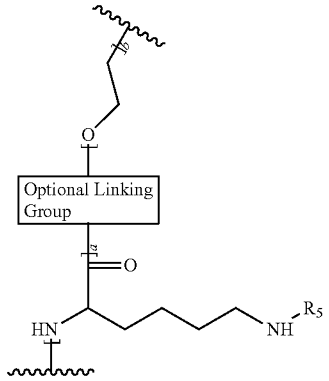

-continued $R_5$ is H or

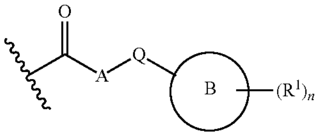

a and b indicate repeating units indicates a point of attachment to another atom or group A particular polyethylene glycol polylysine of formula (ID) is for example

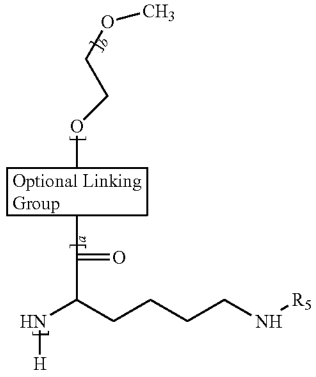

$R_5$ is H or

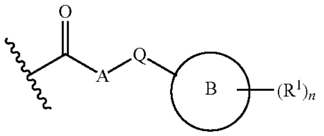

a and b indicate repeating units indicates a point of attachment to another atom or group In any embodiment where polyethylene glycol polylysine is mentioned this may be a polyethylene glycol polylysine comprising a substructure of the formula (IE):

(IE)

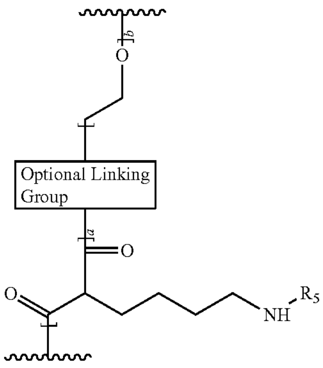

-continued $R_5$ is H or

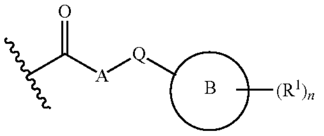

a and b indicate repeating units indicates a point of attachment to another atom or group A particular polyethylene glycol polylysine of formula (IE) is for example

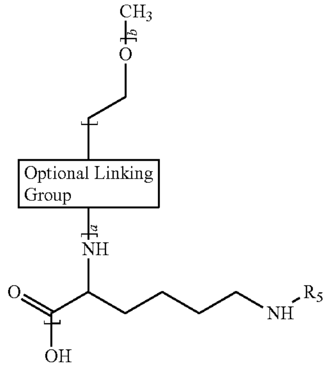

$R_5$ is H or

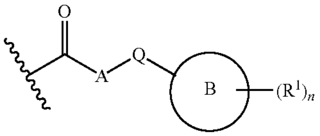

a and b indicate repeating units indicates a point of attachment to another atom or group In any embodiment where polyethylene glycol polylysine is mentioned this may be a polyethylene glycol polylysine comprising a substructure of the formula (IF):

(IF)

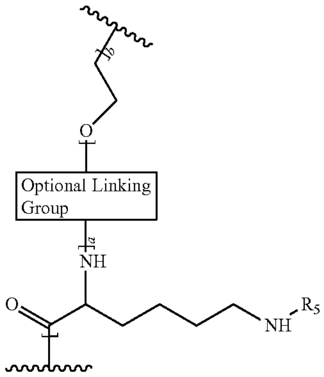

-continued $R_5$ is H or

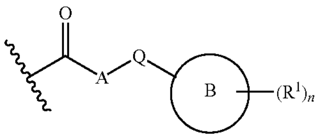

a and b indicate repeating units indicates a point of attachment to another atom or group A particular polyethylene glycol polylysine of formula (IF) is for example

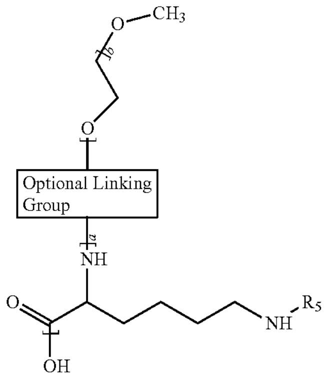

$R_5$ is H or

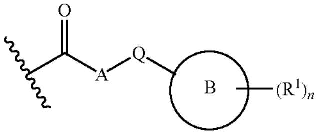

a and b indicate repeating units indicates a point of attachment to another atom or group In any embodiment where polyethylene glycol polylysine is mentioned there may be modifications at one of the terminal ends, or the terminal ends may be hydrogen. A suitable modification for the terminal end of the polyethylene glycol, is for example $C_{1-4}$alkyl, e.g. methyl; or $C_{1-4}$alkoxy, e.g. methoxy.

In any embodiment where PEG is mentioned, the PEG may have a reactive group on the terminal end that is not attached to the polylysine. Suitable reactive groups include maleimide, azide, alkyne (e.g. $C_{2-6}$alkyne), and cyclopentadiene. This reactive group can be used to attach species such as radiolabels, dyes, and cell targeting ligands before or after PEG conjugation to the polypeptide.

In any embodiment where polyethylene glycol polylysine is mentioned there may be modifications at both terminal ends.

In any embodiment where polyethylene glycol polylysine is mentioned there may be a linking group between the polyethylene glycol and the polylysine polymer. A suitable linking group is $C_{1-4}$alkylamino, for example —$CH_2$—$CH_2$—NH—, forming for example a PEG-$CH_2$—$CH_2$—NH-PL polypeptide or a PEG-NH—$CH_2$—$CH_2$—PL polypeptide; or $C_{1-4}$alkylene, for example —$CH_2$—$CH_2$—, forming for example a PEG-$CH_2$—$CH_2$—PL polypeptide.

In any embodiment where PEG is mentioned, this may refer to a polymer with a molecular weight range between 0.5-30 kDa.

In any embodiment where PEG is mentioned, this may refer to a polymer with a molecular weight range between 2-20 kDa.

In any embodiment where PEG is mentioned, this may refer to a polymer with a molecular weight range between 4-11 kDa.

In any embodiment where PEG is mentioned, this may refer to a polymer with a molecular weight range between 1-6 kDa.

In any embodiment where PEG is mentioned, this may refer to a polymer with a molecular weight range of about 2 kDa.

In any embodiment where PEG is mentioned, this may refer to a polymer with a molecular weight range of about 5 kDa.

In any embodiment where PEG is mentioned, this may refer to a polymer with a molecular weight range of about 10 kDa.

In any embodiment where polylysine is mentioned, this may refer to a polyethylene glycol poly-D-lysine.

In any embodiment where polylysine is mentioned, this may refer to a polyethylene glycol poly-L-lysine.

In any embodiment where polylysine is mentioned, this may refer to a polyethylene glycol $_{20}$ poly-L/D-lysine.

In any embodiment where a polylysine is mentioned, this may refer to a polyethylene glycol polylysine comprising 2-1000 lysine residues.

In any embodiment where a polylysine is mentioned, this may refer to a polyethylene glycol polylysine comprising 2-1000 modified lysine residues.

In any embodiment where a polylysine is mentioned, this may refer to a polyethylene glycol polylysine comprising 10-500 lysine residues.

In any embodiment where a polylysine is mentioned, this may refer to a polyethylene glycol polylysine comprising 10-500 modified lysine residues.

In any embodiment where a polylysine is mentioned, this may refer to a polyethylene glycol polylysine comprising 20-100 lysine residues.

In any embodiment where a polylysine is mentioned, this may refer to a polyethylene glycol polylysine comprising 20-100 modified lysine residues.

In any embodiment where a polylysine is mentioned, this may refer to a polyethylene glycol polylysine comprising 20-50 lysine residues.

In any embodiment where a polylysine is mentioned, this may refer to a polyethylene glycol polylysine comprising 20-50 modified lysine residues.

In any embodiment where a polylysine is mentioned, this may refer to a polyethylene glycol polylysine comprising 25-40 lysine residues.

In any embodiment where a polylysine is mentioned, this may refer to a polyethylene glycol polylysine comprising 25-40 modified lysine residues.

Pharmaceutically Active Agents

The compositions and methods described herein are suitable for delivering pharmaceutically active agents. A pharmaceutically active agent is any substance able to exert a pharmacological effect on a human or animal body leading to a therapeutic outcome.

In any embodiment where a pharmaceutically active agent is mentioned, the pharmaceutically active agent may be selected from genetic material, chemically modified nucleic acids, therapeutic peptides, chemotherapy agents, proteins, protein conjugates, imaging agents, protein nucleic acids related to CRISPR technology, and natural virus components such as capsids, or enzymes.

In any embodiment where a pharmaceutically active agent is mentioned, the pharmaceutically active agent may be selected from genetic material.

In any embodiment where a pharmaceutically active agent is mentioned, the pharmaceutically active agent may be selected from genetic material such as DNA or RNA.

In any embodiment where DNA is mentioned this may be plasmid, linear DNA, single stranded DNA, minimalized vectors such as mini-circles and mini-strings, folded DNA including hairpin and cruciform DNA, and viral derived DNA.

In any embodiment where RNA is mentioned this may be mRNA or siRNA.

In any embodiment where a pharmaceutically active agent is mentioned, the pharmaceutically active agent may be selected from DNA.

In any embodiment where a pharmaceutically active agent is mentioned, the pharmaceutically active agent may be selected from RNA.

In any embodiment where a pharmaceutically active agent is mentioned, the pharmaceutically active agent may be selected from chemically modified nucleic acids.

In any embodiment where a pharmaceutically active agent is mentioned, the pharmaceutically active agent may be selected from therapeutic peptides.

In any embodiment where a pharmaceutically active agent is mentioned, the pharmaceutically active agent may be selected from chemotherapy agents.

In any embodiment where a pharmaceutically active agent is mentioned, the pharmaceutically active agent may be selected from proteins.

In any embodiment where a pharmaceutically active agent is mentioned, the pharmaceutically active agent may be selected from protein conjugates.

In any embodiment where a pharmaceutically active agent is mentioned, the pharmaceutically active agent may be selected from imaging agents.

In any embodiment where a pharmaceutically active agent is mentioned, the pharmaceutically active agent may be selected from protein nucleic acids related to CRISPR technology.

In any embodiment where a pharmaceutically active agent is mentioned, the pharmaceutically active agent may be selected from natural virus components such as capsids, or enzymes.

In any embodiment where a pharmaceutically active agent is mentioned, the pharmaceutically active agent may be selected from nucleic acids (i.e. plasmids and mRNA) that encode therapeutic proteins such as monoclonal antibodies, for example, abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, and ustekinumab; enzymes, for example, agalsidase beta, imiglucerase, velaglucerase alfa, taliglucerase, alglucosidase alfa, alglucosidase alfa, laronidase, idursulfase intravenous, and galsulfase; growth factors; and cytokines, for example IL-2 and IFN-α.

In any embodiment where a pharmaceutically active agent is mentioned, the pharmaceutically active agent may be selected from nucleic acids (i.e. plasmids and mRNA) that encode therapeutic proteins such as monoclonal antibodies; enzymes; growth factors; and cytokines.

In any embodiment where a pharmaceutically active agent is mentioned, the pharmaceutically active agent may be selected from nucleic acids (i.e. plasmids and mRNA) that encode monoclonal antibodies.

In any embodiment where a pharmaceutically active agent is mentioned, the pharmaceutically active agent may be selected from nucleic acids (i.e. plasmids and mRNA) that encode monoclonal antibodies selected from abciximab, adalimumab, alefacept, alemtuzumab, basiliximab, belimumab, bezlotoxumab, canakinumab, certolizumab pegol, cetuximab, daclizumab, denosumab, efalizumab, golimumab, inflectra, ipilimumab, ixekizumab, natalizumab, nivolumab, olaratumab, omalizumab, palivizumab, panitumumab, pembrolizumab, rituximab, tocilizumab, trastuzumab, secukinumab, and ustekinumab.

In any embodiment where a pharmaceutically active agent is mentioned, the pharmaceutically active agent may be selected from nucleic acids (i.e. plasmids and mRNA) that encode enzymes.

In any embodiment where a pharmaceutically active agent is mentioned, the pharmaceutically active agent may be selected from nucleic acids (i.e. plasmids and mRNA) that encode enzymes selected from agalsidase beta, imiglucerase, velaglucerase alfa, taliglucerase, alglucosidase alfa, alglucosidase alfa, laronidase, idursulfase intravenous, and galsulfase.

In any embodiment where a pharmaceutically active agent is mentioned, the pharmaceutically active agent may be selected from nucleic acids (i.e. plasmids and mRNA) that encode growth factors.

In any embodiment where a pharmaceutically active agent is mentioned, the pharmaceutically active agent may be selected from nucleic acids (i.e. plasmids and mRNA) that encode cytokines.

In any embodiment where a pharmaceutically active agent is mentioned, the pharmaceutically active agent may be selected from nucleic acids (i.e. plasmids and mRNA) that encode cytokines selected from IL-2 and IFN-α.

In any embodiment where a pharmaceutically active agent is mentioned, the pharmaceutically active agent may be selected from siRNA.

In any embodiment where a pharmaceutically active agent is mentioned, the pharmaceutically active agent may be selected from siRNA used to reduce protein expression in applications including regulation of oncogene, growth factor, and cytokine expression.

Formulation

In one embodiment there is provided a pharmaceutical delivery system which comprises a polypeptide comprising one or more modified lysine residues as described herein. A pharmaceutical delivery system is a delivery system that may be employed to deliver a pharmaceutically active agent into a human or animal body.

In one embodiment there is provided the use of one or more modified lysine residues as described herein in a pharmaceutical delivery system.

In one embodiment there is provided the use of a polypeptide as described herein in a pharmaceutical delivery system.

In one embodiment there is provided a polypeptide as described herein for use as a pharmaceutical delivery system.

In one embodiment there is provided a delivery system for a pharmaceutically active agent which comprises a polypeptide comprising one or more modified lysine residues as described herein.

Polypeptides comprising the modified lysine residues as described herein and a pharmaceutically active agent may be combined while gently mixing in a physiologically isotonic buffer (e.g. 5% trehalose or sucrose, 20 mM HEPES, or phosphate buffered saline (PBS)) to form nanoparticles. These formulations may be delivered immediately, stored at 4° C., or lyophilized for long term storage.

Polypeptides comprising the modified lysine residues as described herein may be prepared in a ao form suitable for oral administration, for example as a tablet or capsule, for parenteral injection (including intravenous, subcutaneous, intradermal, intramuscular, intravascular or infusion), for topical administration as an ointment or cream or for rectal administration as a suppository. In particular, polypeptides comprising the modified lysine residues as described herein may be prepared in a form suitable for injection e.g. by intravenous, subcutaneous, intradermal, or intramuscular injection.

Uses

Polypeptides comprising one or more modified lysine residues as described herein may be used to deliver a pharmaceutically active agent suitable to treat a broad range of ailments including metabolic disorders, immunological disorders, hormonal disorders, cancer, hematological disorders, genetic disorders, infectious disease, cardiac disease, bone disorders, respiratory disorders, neurological disorders, adjunct therapy, eye disorders, malabsorption disorders. Therapeutic application may include: systemic expression of proteins (i.e. antibodies for virus treatment) or targeted delivery (i.e. metastatic tumours, in vivo CAR-T).

In one embodiment there is provided a pharmaceutical delivery system which comprises a polypeptide comprising one or more modified lysine residues as described herein for use in therapy.

In one embodiment there is provided a delivery system for a pharmaceutically active agent which comprises a polypeptide comprising one or more modified lysine residues as described herein for use in therapy.

In one embodiment there is provided a pharmaceutical delivery system which comprises a polypeptide comprising one or more modified lysine residues as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a delivery system for a pharmaceutically active agent which comprises a polypeptide comprising one or more modified lysine residues as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a delivery system for a pharmaceutically active agent which comprises a polypeptide comprising one or more modified lysine residues as described herein for use in gene therapy.

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

Pharmaceutical Compositions

In one embodiment there is provided a pharmaceutical composition which comprises a polypeptide comprising one or more modified lysine residues as described herein.

In one embodiment there is provided a pharmaceutical composition which comprises a polypeptide comprising one or more modified lysine residues as described herein and a pharmaceutically active agent.

In one embodiment there is provided a pharmaceutical composition comprises a polypeptide comprising one or more modified lysine residues as described herein for use in therapy.

In one embodiment there is provided a pharmaceutical composition comprises a polypeptide comprising one or more modified lysine residues as described herein and a pharmaceutically active agent for use in therapy.

In one embodiment there is provided a pharmaceutical composition comprises a polypeptide comprising one or more modified lysine residues as described herein for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a pharmaceutical composition comprises a polypeptide comprising one or more modified lysine residues as described herein and a pharmaceutically active agent for use in the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided a pharmaceutical composition comprises a polypeptide comprising one or more modified lysine residues as described herein and a pharmaceutically active agent for use in gene therapy.

In one embodiment there is provided a pharmaceutical composition comprises a polypeptide comprising one or more modified lysine residues as described herein for use in gene therapy.

Methods of Treatment

In one embodiment there is provided a method of treating metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders in a warm-blooded animal, such as man, which comprises administering to said animal an effective amount of a pharmaceutical composition comprising a polypeptide comprising one or more modified lysine residues as described herein.

In one embodiment there is provided a method of treating metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders in a warm-blooded animal, such as man, which comprises administering to said animal an effective amount of a pharmaceutical composition comprising a polypeptide comprising one or more modified lysine residues as described herein and a pharmaceutically active agent.

In one embodiment there is provided a method of gene therapy which comprises administering a polypeptide comprising one or more modified lysine residues as described herein.

In one embodiment there is provided a method of gene therapy which comprises administering a polypeptide comprising one or more modified lysine residues as described herein and a pharmaceutically active agent.

Use of Pharmaceutical Compositions

In one embodiment there is provided the use of a pharmaceutical composition which comprises a polypeptide comprising one or more modified lysine residues as described herein in the manufacture of a medicament for the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided the use of a pharmaceutical composition which comprises a polypeptide comprising one or more modified lysine residues as described herein and a pharmaceutically active agent in the manufacture of a medicament for the treatment of metabolic disorders, immunological disorders, hormonal disorders, cancer, hematological disorders, genetic disorders, infectious disease, cardiac disease, bone disorders, respiratory disorders, neurological disorders, adjunct therapy, eye disorders, or malabsorption disorders.

In one embodiment there is provided the use of a pharmaceutical composition which comprises a polypeptide comprising one or more modified lysine residues as described herein in gene therapy.

In one embodiment there is provided the use of a pharmaceutical composition which comprises a polypeptide comprising one or more modified lysine residues as described herein and a pharmaceutically active agent in gene therapy.

Kits

In one embodiment there is provided a kit comprising:

a) a polypeptide comprising one or more modified lysine residues as described herein in a first unit;

b) a pharmaceutically active agent in a second unit; and c) container means for containing said first and second units.

In one embodiment there is provided a kit comprising:

a) a polypeptide comprising one or more modified lysine residues as described herein in a first unit;

b) a pharmaceutically active agent in a second unit; and c) container means for containing said first and second units.

d) instructions for use.

BRIEF DESCRIPTION OF THE FIGURES

FIG. 4 Shows the results from Nanoparticle Transfections Experiment 3). C2C12 Myotube Transfection. Normalized luminescence after cells were treated with PLL nanoparticles encoding luciferase under the following conditions: (A) OPTI-MEM, (B), OPTI-MEM supplemented with 100 μM chloroquine, (C) media supplemented with FBS and (D) media supplemented with 100 μM chloroquine and 10% FBS.

EXAMPLES

Abbreviations Used Herein

Figure 1A:
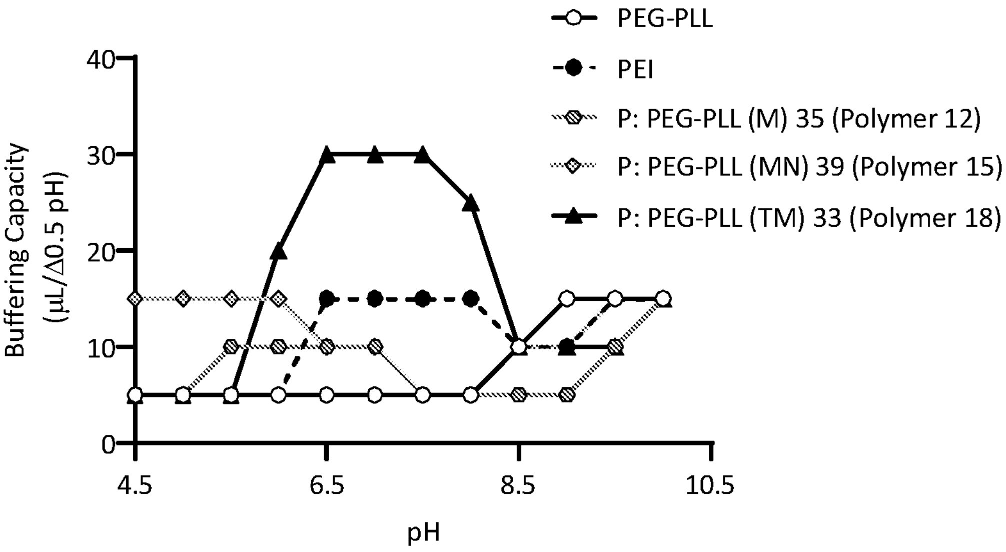
FIG. 1A: Shows the results from Buffering Experiment 1a): Acid-Base Titration. The buffering properties in the pH range of 4.5-6.5 of the indicated polymers in solution are depicted in the graph.

The following shorthand is used herein to denote a particular polymer or nanoparticie:

"P" or "N": "PLL" or "PEG-PLL" (modification) % modification e.g. "P: PLL(M) 33" and "N: PEG-PLL(TM) 30".

Key:

P: Polymer;

N: Nanoparticle;

PLL: Poly-L-lysine is the polypeptide;

PEG-PLL: The polypeptide comprises both a polyethylene glycol polymer and a poly-L-lysine polypeptide;

Modification: is the modification at the ε-nitrogen of the lysine (as depicted in formula (I)) according to the following key "M", "MN" or "TM":

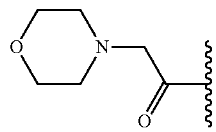

M

-continued

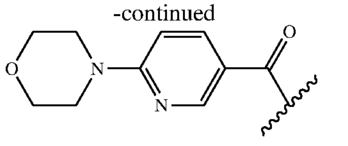

MN

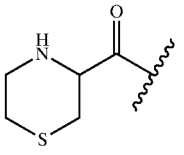

TM

% Modification: refers to:

$$\frac{\text{modified } \varepsilon\text{-nitrogens}}{\text{modified } \varepsilon\text{-nitrogens} + \text{unmodified } \varepsilon\text{-nitrogens}} \times 100\%$$

Method 1

Synthesis of 1-{[(morpholin-4-yl)acetyl]oxy}pyrrolidine-2,5-dione

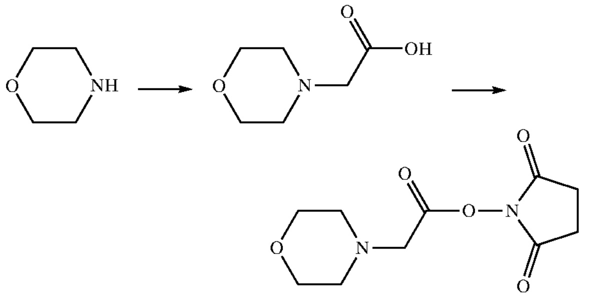

(Morpholin-4-yl)acetic acid (1 & 6.89 mmol) was dissolved in dichloromethane (DCM) (25 mL) and N-hydroxysuccinimide (NHS) (872 mg, 7.58 mmol) and N-ethyl-N'-(3-dimethylaminopropyl)carbodiimide hydrochloride (EDC·HCl) (1.60 & 8.35 mmol) were added. The reaction was stirred at room temperature for 1 h before filtering through a 2"×3" pad of silica gel. The pad was washed with DCM (3×25 mL) and the filtrate and washings were combined and concentrated to give 1-{[(morpholin-4-yl)acetyl]oxy}pyrrolidine-2,5-dione (1.3 & 78%) as white solid. $^1$H NMR (300 MHz, $CDCl_3$) δ 3.75 (d, J=3.6 Hz, 4H), 3.57 (s, 2H), 2.85 (s, 4H), 2.67 (d, J=4.2 Hz, 4H); MS (ESI) calc.:242.09, obs.:243.3 (M+1).

Method 2

Synthesis of 1-{[6-(morpholin-4-yl)pyridine-3-carbonyl]oxy}pvrrolidine-2,5-dione

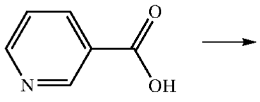

-continued

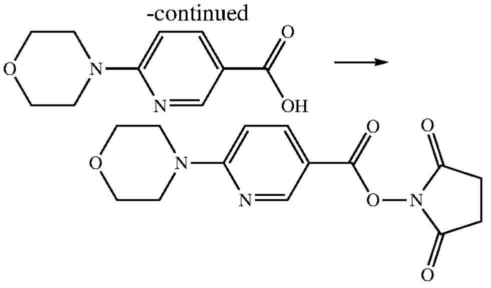

6-(Morpholin-4-yl)pyridine-3-carboxylic acid (350 m& 1.68 mmol) was dissolved in DCM (25 mL) at room temperature with stirring. NHS (213 mg, 1.85 mmol) was added followed by EDC·HCl ((418 mg, 2.18 mmol). The reaction mixture was stirred at room temperature for 1 h and then filtered through a 2"×3" pad of silica gel. The pad was washed with DCM (3×25 mL) and ethyl acetate (25 mL). The filtrate and washings were combined and concentrated to give 1-{[6-(morpholin-4-yl)pyridine-3-carbonyl]oxy}pyrrolidine-2,5-dione (325 mg, 63%) as a white solid. $^1$H NMR (300 MHz, $CDCl_3$) δ 8.89 (s, 1H), 8.07 (dd, J=9.3 Hz, 1.5 Hz, 1H), 6.60 (d, J=9.3 Hz, 1H), 3.80 (d, J=4.2 Hz, 4H) 3.72 (d, J=4.2 Hz, 4H), 2.89 (s, 4H). MS (ESI) calc.: 305.1, obs.: 306.3 (M+1).

Method 3

Synthesis of tert-butyl 3-{[(2,5-dioxopyrrolidin-1-yl)oxy]carbonyl}thiomorpholine-4-carboxylate

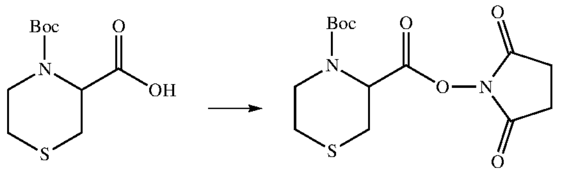 [SMILES: CC(C)(C)OC(=O)N1CCSCC1C(=O)O ; CC(C)(C)OC(=O)N1CCSCC1C(=O)ON1C(=O)CCC1=O]

4-(tert-Butoxycarbonyl)thiomorpholine-3-carboxylic acid (1 & 4.04 mmol) was dissolved in DCM (25 mL) at room temperature with stirring. NHS (511 m& 4.44 mmol) was added followed by addition of EDC·HCl (1.01 & 5.25 mmol). The reaction mixture was stirred at room temperature for 1 h and then filtered through a 2"×3" pad of silica gel. The pad was washed with DCM (3×25 mL) and the filtrate and washings were combined and concentrated to give tert-butyl 3-{[(2,5-dioxopyrrolidin-1-yl)oxy]carbonyl}thiomorpholine-4-carboxylate (1.3 & 93.4%) as a white solid. $^1$H NMR (300 MHz, $CDCl_3$) δ 5.38 (br s, 1H), 4.43-4.22 (m, 1H), 3.46-3.21 (m, 1H), 3.19-3.10 (m, 1H), 3.06-2.97 (m, 1H), 2.85 (s, 4H), 2.81-2.62 (m, 1H), 2.61-2.42 (m, 1H), 1.47 (s, 9H). MS (ESI) calc.: 345.4 (M+1).

Method 4

Synthesis of N2-(((9H-fluoren-9-yl)methoxylcarbonyl)-N6-(6-morpholinonicotinoyl)-L-lysine

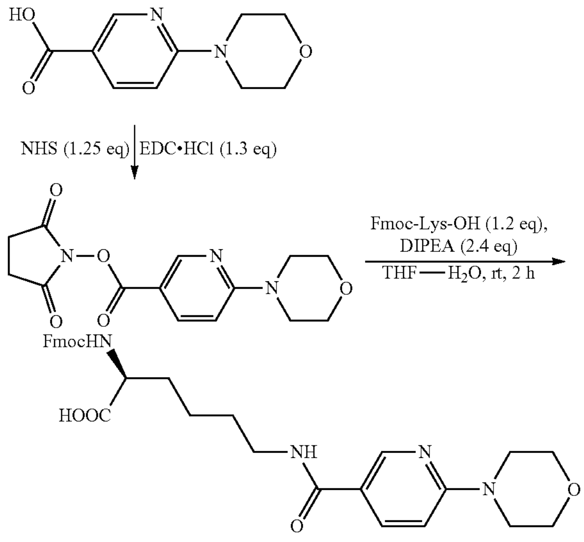

Fluorenylmethyloxycarbonyl chloride L-lysine (Fmoc-Lys-OH) (15.3 & 41.53 mmol, 1.2 eq) was dissolved in THF-water (1:1, 800 mL) under mechanical stirring at room temperature. A solution of the above prepared ester (Method 2) in DCM was added in one portion followed by DIPEA (10.73 g, 82.99 mmol, 2.4 eq). The reaction was stirred further at room temperature until consumption of the starting material (TLC, 2 h), then ethyl acetate (EtOAc) (250 mL) was added. The mixture was acidified with HQ (1M, 200 mL), poured into a separatory funnel, and the layers separated. The aqueous layer was extracted with EtOAc (2×250 mL). The organic layers were combined, washed with brine (200 mL), dried over anhydrous $Na_2SO_4$, filtered, and concentrated under vacuum. The crude product was obtained as light brown coloured oily residue which was dissolved in THF, adsorbed on silica gel and purified by flash chromatography over a column (7"×3") of silica gel. The column was washed with 50% ethyl acetate in hexanes and 100% ethyl acetate to elute the product under vacuum suction. The fractions containing the required product were combined and concentrated under vacuum to provide N2-(((9H-fluoren-9-yl)methoxy)carbonyl)-N6-(6-morpholinonicotinoyl)-L-lysine (12.6 g, 65%) as off-white coloured solid. $^1H$ NMR (500 MHz, CDC13) δ 9.26 (br s, 1H), 8.62 (d, J=1.5 Hz, 1H), 7.93 (dd, J=2.5, 9 Hz, 1H), 7.71 (d, J=7.5 Hz, 2H), 7.53 (dd, J=4.5, 7.5 Hz, 2H), 7.35 (t, J=7.5 Hz, 2H), 7.23 (q, J=6.5 Hz, 2H), 6.59 (t, J=5 Hz, 1H), 6.48 (d, J=9 Hz, 1H), 5.99 (d, J=8 Hz, 1H), 4.41 (dd, J=7.5, 12.5 Hz, 1H), 4.31 (dd, J=12, 18 Hz, 2H), 4.15 (d, J=7 Hz, 1H), 3.71 (t, =4.5 Hz, 4H), 3.56-3.32 (m, 6H), 1.98-1.87 (m, 1H), 1.86-1.75 (m, 1H), 1.71-1.57 (m, 2H), 1.56-1.39 (m, 2H) ppm; 13C NMR (125 MHz, $CDCl_3$) δ 175.2, 166.6, 159.9, 156.6, 146.9, 144.1, 143.9, 141.4, 137.7, 127.9, 127.3, 125.3, 120.1, 119.5, 106.3, 67.2, 66.6, 53.8, 47.3, 45.3, 39.5, 32.0, 28.9, 22.4 ppm; MS (ESI) Exact mass cald. for C31H34N4O6 [M+H]+: 559.26, found: 559.35.

Example 1

Synthesis of (2S)-2-amino-6-{[6-(morpholin-4-yl)pyridine-3-carbonyl]amino}hexanoic acid (N6-(6-morpholinonicotinoyl)-L-lysine)

Method 1:

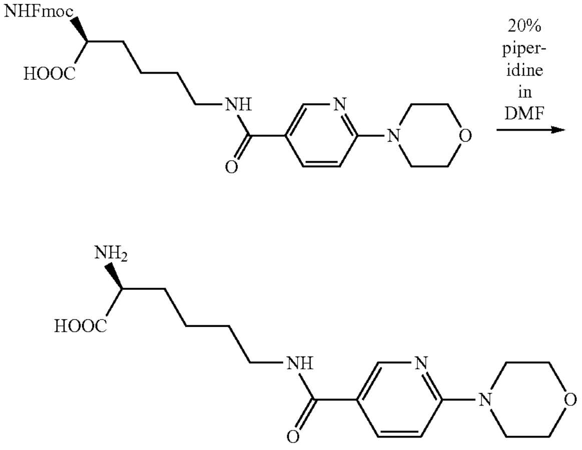

The Fmoc protecting group of N2-(((9H-fluoren-9-yl)methoxy)carbonyl)-N6-(6-morpholinonicotinoyl)-L-lysine (Method 4) may be removed by standard procedures known in the art for example using 20% piperidine in DMF.

Method 2:

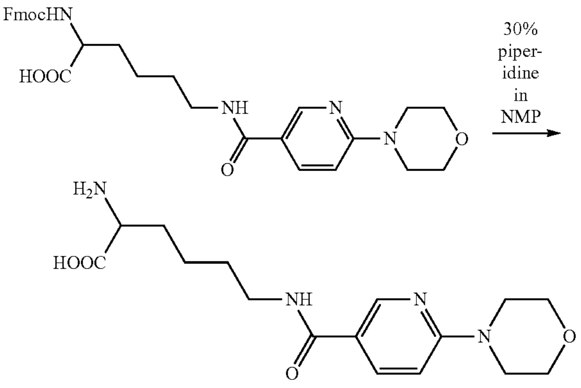

The modified lysine was dissolved in 700 μL of NMP (15 mg, 26.87 μmol. 300 μL piperidine was subsequently added to the solution (Piperidine:NMP=7:3; 1 mL) while stirring. The reaction was stirred at room temperature for 30 minutes. The modified lysine was subsequently precipitated and washed 3 times in cold diethyl ether (10 mL) using centrifugation (4000 g, 10 minutes, 4° C.). $^1H$ NMR (500 MHz, $CDCl_3$) was used to confirm Fmoc removal 1H NMR (500 MHz, CDI3) δ11.89 (s, 1H), 8.85 (dd, 1H), 7.89 (dd, 1H), 7.34 (dd, 1H), 3.52-3.71 (m, 8H), 3.35 (t, 1H), 2.72-2.61 (t, 2H), 2.01-1.57 (m, 6H) ppm. MS (ESI) Exact mass cald. [M+H2O]+: 352.55, found: 352.04.

Method 5

Synthesis of N2-(((9H-fluoren-9-yl)methoxy)carbonyl)-N6-(4-(tert-butoxvcarbonyl)thiomoroholine-3-carbonyl)-L-lysine

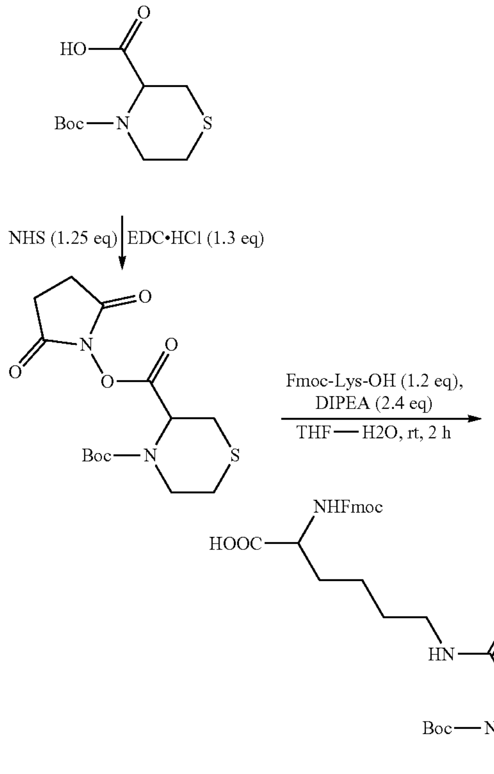

Fmoc-L-Lys-OH (8.94 & 24.26 mmol, 1.2 eq) was dissolved in THE-water (1:1, 800 mL) under mechanical stirring at room temperature. A solution of the above prepared activated ester (Method 3) in DCM was added in one portion followed by DIPEA (6.27 & 48.53 mmol, 2.4 eq). The reaction was stirred further at room temperature until consumption of the starting material (TLC, 2 h), then EtOAc (250 mL) was added. The mixture was acidified with HCl (1 M, 200 mL), poured into a separatory funnel, and the layers separated. The aqueous layer was extracted with EtOAc (2×250 mL). The organic layers were combined, washed with brine (200 mL), dried over anhydrous Na2SO4, filtered, and concentrated under vacuum. The crude product was obtained as light yellow coloured oily residue which was dissolved in DCM, adsorbed on silica gel and purified by flash chromatography over a column (7"×3") of silica gel. The column was washed with 50%-70% ethyl acetate in hexanes to elute the product under vacuum suction. The fractions containing the required product were combined and concentrated under vacuum to provide N2-(((9H-fluoren-9-yl)methoxy)carbonyl)-N6-(4-(tert-butoxycarbonyl) thiomorpholine-3-carbonyl)-L-lysine (9.1 & 75%) as off-white coloured solid. $^{1}H$ NMR (500 MHz, $CDCl_3$) δ7.75 (d, J=7.5 Hz, 2H), 7.63-7.51 (m, 2H), 7.38 (t, J=7.5 Hz, 2H), 7.29 (t, J=7.5 Hz, 2H), 5.71 (dd, J=7.5, 23 Hz, 1H), 4.97 (br s, 1H), 4.57-4.23 (m, 4H), 4.20 (t, J=7 Hz, 1H), 3.51-3.18 (m, 3H), 3.17-2.96 (br s, 1H), 2.77 (d, J=12.5 Hz, 1H), 2.70-2.58 (m, 1H), 2.38 (d, J=12.5 Hz, 1H), 1.98-1.86 (m, 1H), 1.85-1.73 (m, 1H), 1.66-1.53 (m, 2H), 1.46 (br s, 12H) ppm; 13C NMR (125 MHz, CDC13) δ 175.0, 156.4, 155.8, 143.9, 141.4, 127.9, 127.3, 125.3, 120.1, 67.3, 60.6, 53.8, 47.3, 39.2, 31.5, 29.1, 28.5, 26.7, 22.3 ppm; MS (ESI) Exact mass cald. for $C_{31}H_{39}N_3O_7S$ [M+Na]+: 620.24, found: 620.35.

Example 2

Synthesis (2S)-2-amino-6-[(thiomorpholine-3-carbonyl)amino]hexanoic acid (N6-(thiomorpholine-3-carbonyl)-L-lysine)

Method 1:

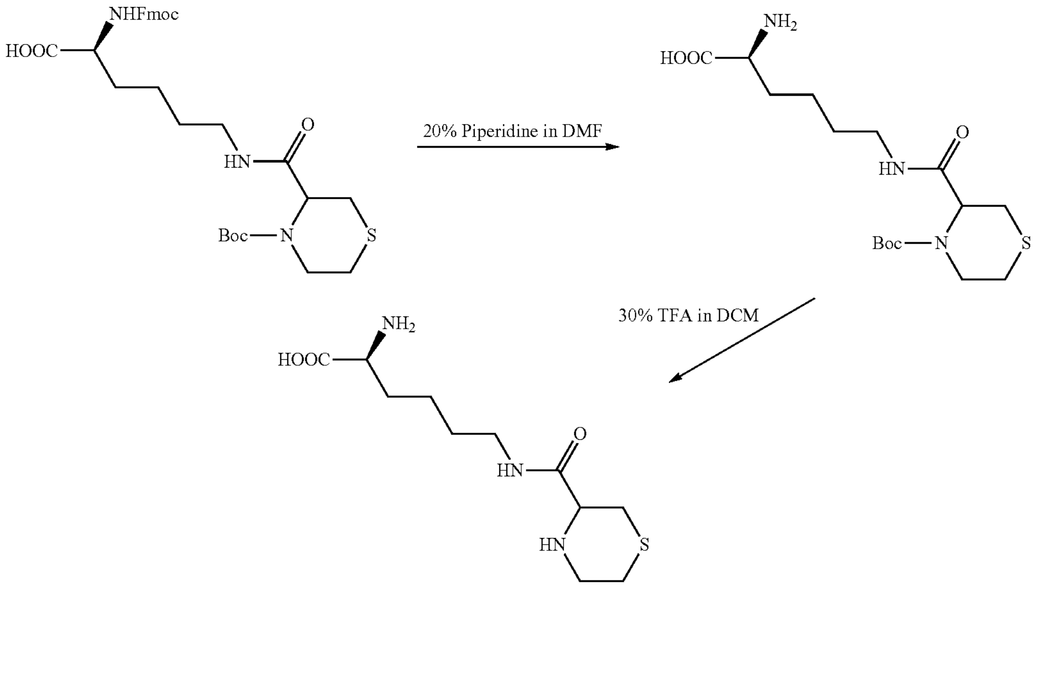

The Fmoc protecting group of N2-(((9H-fluoren-9-yl)methoxy)carbonyl)-N6-(4-(tert-butoxycarbonyl)thiomorpholine-3-carbonyl)-L-lysine (Method 5) may be removed by standard procedures known in the art for example using 20% piperidine in DMF. Similarly, the Boc protecting group may be removed by standard procedures known in the art for example using 30% TFA in DCM.

Method 2:

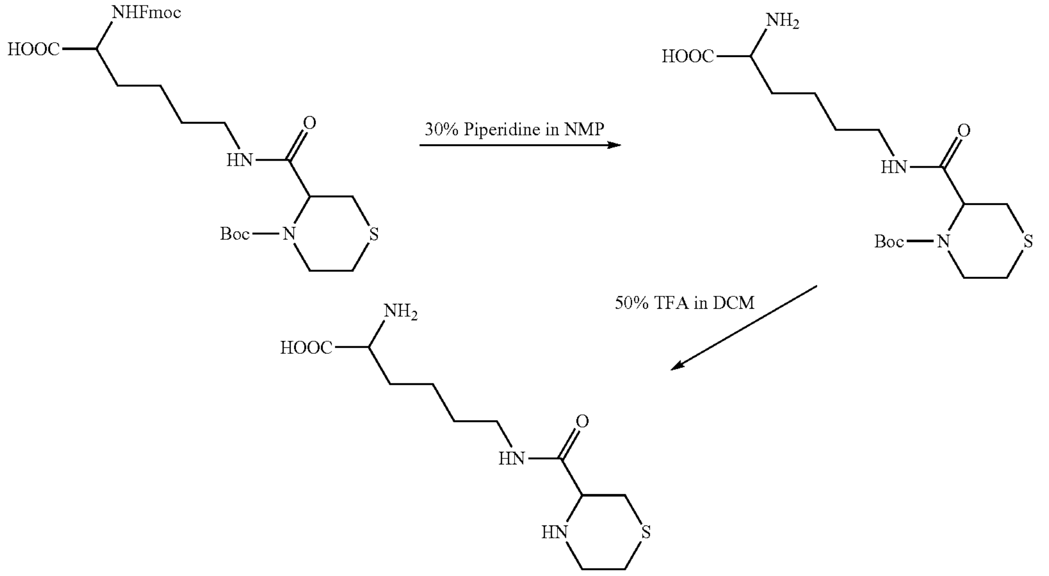

The modified lysine was dissolved in 700 μL of NMP (15 mg, 25.12 μmol. 300 μL piperidine was subsequently added to the solution (Piperidine:NMP=7:3; 1 mL) while stirring. The reaction was stirred at room temperature for 30 minutes to remove the Fmoc protectant group. The modified lysine was subsequently precipitated and washed 3 times in cold diethyl ether (10 mL) using centrifugation (4000 g, 10 minutes, 4° C.). After air drying overnight, the product was dissolved in 50% TFA:DCM (1 mL) and stirred at room temperature for 15 minutes. The TFA:DCM solution was removed using a rotary evaporator and the precipitated and washed 2 times in cold ethyl ether Fmoc removal was confirmed using $^1$H NMR: δ11.56-12.04 (1H, br), 7.34 (s, 1H), 3.65-3.76 (dd, 2H), 3.42 (t, J=7.3 Hz, 1H), 3.01-3.15 (m, 2H), 2.70-2.89 (m, 2H), 2.55-2.61 (t, J=5.6 Hz, 2H), 2.06-2.18 (m, 2H), 1.74-1.85 (m, 2H), 1.58-1.64 (q, 2H) 1.05 (1H, s) ppm and MS (ESI) Exact mass cald. [M+H2O]+: 279.22, found: 279.62.

Method 6

Synthesis of N2(1-{[(morpholin-4-yl)acetyl]oxy}pyrrolidine-2,5-dione)-L-lysine

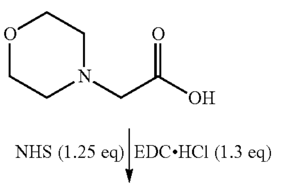

-continued

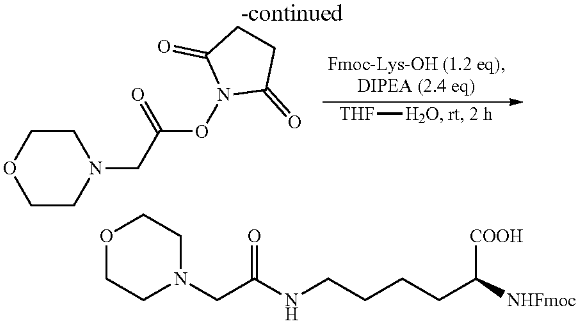

The following procedure could be employed to generate N2(1-{[(morpholin-4-yl)acetyl]oxy}pyrrolidine-2,5-dione)-L-lysine, Fmoc-L-Lys-OH 1.2 eq) may be dissolved in THE-water (1:1, 800 mL) under mechanical stirring at room temperature. A solution of the above prepared activated ester in DCM may be added in one portion followed by DIPEA (2.4 eq). The reaction may be stirred further at room temperature until consumption of the starting material (TLC, 2 h), then EtOAc (250 mL) may be added. The mixture may be acidified with HCl (1 M, 200 mL), poured into a separatory funnel, and the layers separated. The aqueous layer many be extracted with EtOAc (2×250 mL). The organic layers may be combined, washed with brine (200 mL), dried over anhydrous $Na_2SO_4$, filtered, and concentrated under vacuum. The crude product may be dissolved in DCM, adsorbed on silica gel and purified by flash chromatography over a column (7"x3") of silica gel. The column may be washed with 50%-70% ethyl acetate in hexanes to elute the product under vacuum suction. The fractions containing the required product may be combined and concentrated under vacuum to provide N2-(N2(1-{[(morpholin-4-yl)acetyl]oxy}pyrrolidine-2,5-dione)-L-lysine.

Example 3

Synthesis of (2S)-2-amino-6-[2-(morpholin-4-yl)acetamido]hexanoic acid (N6-(2-morpholinoacetyl)-L-lysine)

Method 1:

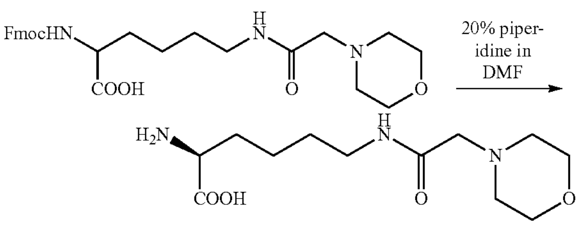

The Fmoc protecting group of N2(1-{[(morpholin-4-yl)acetyl]oxy}pyrrolidine-2,5-dione)-L-lysine (Method 6) may be removed by standard procedures known in the art for example using 20% piperidine in DMF.

Method 2:

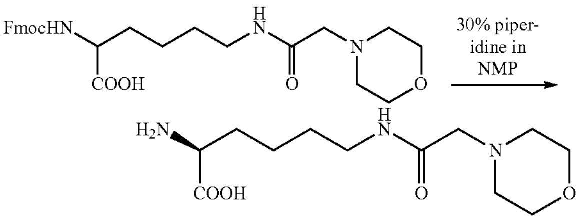

The modified lysine was dissolved in 700 μL of NMP (15 mg, 25.02 limo. 300 μL piperidine was subsequently added to the solution (Piperidine:NMP=7:3; 1 mL) while stirring. The reaction was stirred at room temperature for 30 minutes. The modified lysine was subsequently precipitated and washed 3 times in cold diethyl ether (10 mL) using centrifugation (4000 g, 10 minutes, 4° C.). Fmoc removal was confirmed using was confirmed using H-NMR: 1H NMR (500 MHz, CDI3) δ12.01 (br s, 1H), 3.62-3.74 (m, 4H), 3.40 (t, 1H), 3.29 (s, 2H), 3.10 (t, 1H), 2.59-2.70 (m, 4H), 1.88-2.01 (m, 2H), 1.58-1.65 (m, 2H), and 1.46-1.56 (q, 2H) and MS (ESI) Exact mass cald. [M+H2O]+: 273.17, found: 273.33.

Example 4

Poly(L-Lysine) and PEG-Poly(L-Lysine) Polypeptides

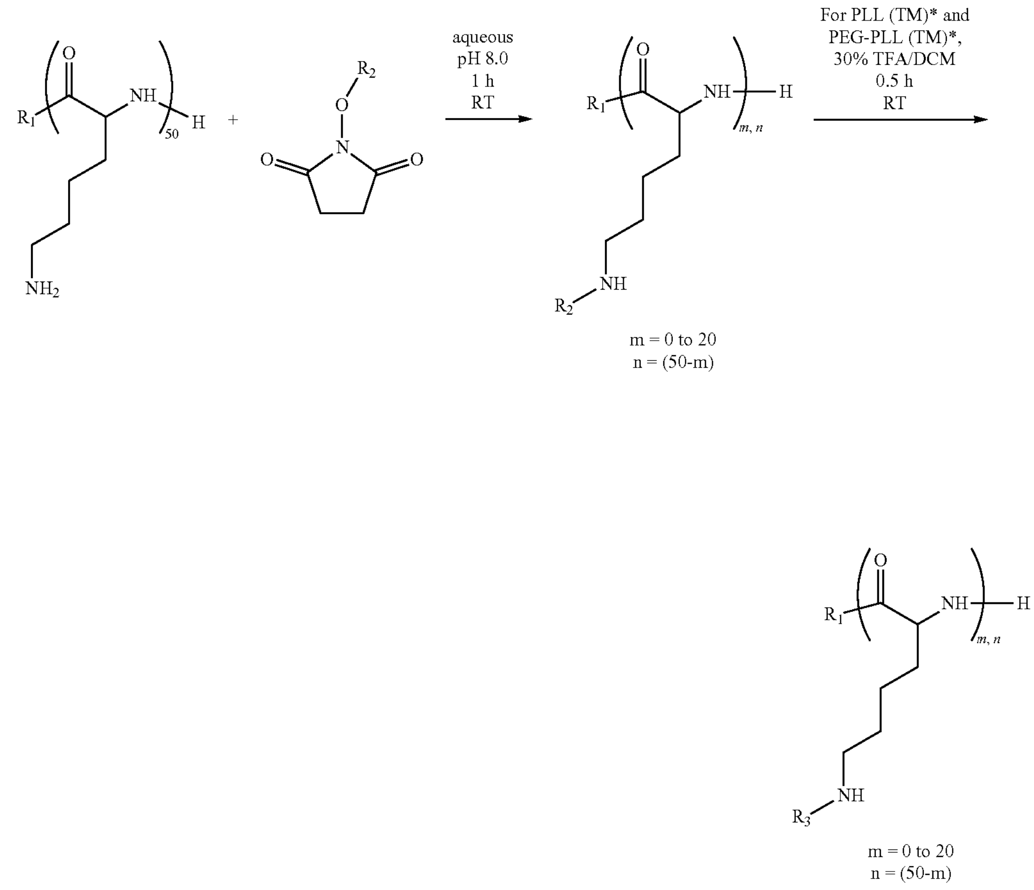

-continued $R_1$ = X polymerization initiator residue or

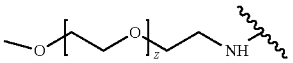

z = ~113
PEG MW ~ 5000 Da $R_{2,n}$ = H $R_{2,m}$ =

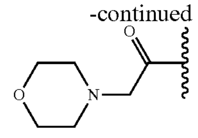

polymer product: PLL(M) or PEG-PLL (M)

or

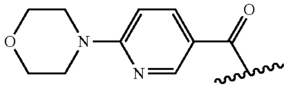

polymer product: PLL(MN) or PEG-PLL (MN)

or

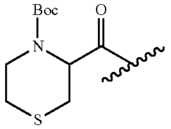

intermediate product: PLL(TM)* or PEG-PLL (TM)*

$R_3$, m =

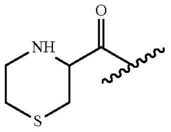

polymer product: PLL(TM) or PEG-PLL (TM)

Modified PEG-PLL and PLL was prepared by reacting the NHS-esters prepared in Methods 1-3 with the corresponding PLL (MW 5000, Alamanda Polymers Inc., Huntsville AL) or PEG-PLL (MW 13000, Alamanda Polymers Inc., Huntsville AL). All polymers were supplied with a polymerisation initiator residue (referred to herein simply as PLL) or MeO-PEG-$(CH_2)_2$—NH— group (referred to herein as PEG-PLL) at the terminal carboxy end of the PLL. PLL (20 mg, 2.5 limo) or PEG-PLL (20 mg, 1.5 μmot) was dissolved in freshly prepared 0.1 M sodium bicarbonate, pH 8.0 (4 mL). 40 mM of the compounds of Methods 1, 2 or 3 were prepared in dimethylacetamide (DMAC) (1.5 molar excess) and added dropwise to the polymer solution while stirring. A series of PLLs with different degrees of modification were prepared by controlling the molar feed ratio of the NHS-esters. Modification reactions were conducted at 12.5 to 50 molar equivalents NHS ester:polymer. The reaction was stirred at room temperature for 1 hour, and non-reacted groups were subsequently removed through dialysis in phosphate buffered saline (PBS) pH 7.4 and then water using a dialysis cassette with a molecular weight cut off (MWCO) of 3.5 kDa. For PLL(TM) and PEG-PLL(TM), the Boc protectant group on the intermediate products (*) was removed using a standard protocol used in prior art through incubation of the lyophilized product in 30% trifluoroacetic acid/DCM for 30 minutes. The degree of lysine modification was determined from the H-NMR spectra recorded in $D_2O$ by peak intensity ratio of β, γ, and δ-methylene protons of Lys ($(CH_2)_3$, δ=1.3-1.9 ppm) to the sum of peak intensities of methylene protons from morpholine rings of morpholine (M) (starting material Method 1) and morpholino-niacin groups (starting material Method 2) (MN) $(CH_2)_2$, δ=3.86 and 2.58 ppm for morpholine and morpholino-niacin and $(CH_2)_2$, δ=3.11 and 3.56 ppm for thiomorpholine (TM) (starting material Method 3), and the results are shown in the table below.

TABLE 1

Modified PLLs and PEG-PLLs

| Polymer # | Polymer Abbreviation | Feed ratio (moles NHS:moles amine) | Modified lysines (%) | Modified lysines | Unmodified lysines |
|---|---|---|---|---|---|
| 1 | P: PLL(M) 24 | 0.25 | 24 | 12 | 38 |
| 2 | P: PLL(M) 37 | 0.50 | 37 | 18.5 | 31.5 |
| 3 | P: PLL(M) 53 | 1 | 53 | 26.5 | 23.5 |
| 4 | P: PLL(MN) 24 | 0.25 | 24 | 12 | 38 |
| 5 | P: PLL(MN) 32 | 0.50 | 32 | 16 | 34 |
| 6 | P: PLL(MN) 51 | 1 | 51 | 25.5 | 24.5 |
| 7 | P: PLL (TM) 21 | 0.25 | 21 | 10.5 | 39.5 |
| 8 | P: PLL (TM) 39 | 0.50 | 39 | 16.5 | 33.5 |
| 9 | P: PLL (TM) 50 | 1 | 50 | 25 | 25 |
| 10 | P: PEG-PLL(M) 24 | 6.25 | 24 | 12 | 38 |
| 12 | P: PEG-PLL(M) 35 | 0.50 | 35 | 17.5 | 32.5 |
| 13 | P: PEG-PLL(M) 63 | 1 | 63 | 31.5 | 18.5 |
| 14 | P: PEG-PLL(MN) 24 | 0.25 | 24 | 12 | 38 |
| 15 | P: PEG-PLL(MN) 39 | 0.50 | 39 | 19.5 | 30.5 |
| 16 | P: PEG-PLL(MN) 65 | 1 | 65 | 32.5 | 17.5 |
| 17 | P: PEG-PLL (TM) 24 | 0.25 | 24 | 12 | 38 |

TABLE 1-continued

| Modified PLLs and PEG-PLLs | | | | | |
|---|---|---|---|---|---|
| Polymer # | Polymer Abbreviation | Feed ratio (moles NHS:moles amine) | Modified lysines (%) | Modified lysines | Unmodified lysines |
| 18 | P: PEG-PLL (TM) 33 | 0.50 | 33 | 16.5 | 33.5 |
| 19 | P: PEG-PLL (TM) 61 | 1 | 61 | 30.5 | 19.5 |

Example 5

Preparation and Characterization of Nanoparticles with Genetic Material

Nanoparticles were prepared by mixing polypeptide and nucleic acid solutions in a neutral buffer. Nanoparticles were assessed using standard techniques including dynamic light scattering (DLS), transmission electron microscopy (TEM), and ethidium bromide exclusion assays to confirm nanoparticle formation.

a) Nanoparticle Preparation

DNA (Gwiz Luciferase; Genlantis, San Diego, CA) (66.6 μg/mL) and polymer solutions were prepared in 20 mM 4-(2-hydroxyethyl)-1-piperazineethanesulfonic acid (HEPES) buffer, pH 7.0. Polymer solutions were prepared with PLL (50 units, Alamanda Polymers, Inc., Huntsville AL), PEG (5K)-PLL (50 units) (Alamanda Polymers, Inc., Huntsville AL) and "P: PLL(M) 29", "P: PLL(MN) 31", "P: PLL(TM) 28", "P: PEG-PLL(M) 33", "P: PEG-PLL(MN) 31" and "P: PEG-PLL(TM) 30" (all prepared by a procedure analogous to Example 4). Polymer solutions also were prepared in HEPES so the ratio of amines (N) in the polymer to phosphates (P) in the DNA backbone (N:P ratio) would be between 0.5 and 10. DNA solutions were subsequently added drop-wise to polymer solutions while gently vortexing to ensure homogenous particles. DNA/polymer nanoparticles were allowed to form at room temperature for 30 minutes. The final concentration of DNA in the nanoparticles solution was 33.3 μg/mL. Initially, complexes were prepared a different N:P ratios (0.5-10) and DNA gel electrophoresis was used to determine the ratio required for nucleic acid condensation.

b) Dynamic Light Scattering (DLS)

DLS data was collected using a ZetaSizer Nano ZS instrument (Malvern Instruments Ltd., Worcester, UK) with a green laser (λ=532 nm) as the incident beam. All measurements were performed at 25° C. at a detection angle of 173'. Nanoparticle samples prepared as described above in 20 mM HEPES buffer (pH 7.4) at 33.3 μg of complexes pDNA/mL were loaded into a low volume ZEN2112 quartz cuvette (12.5 μL). The hydrodynamic diameter and polydispersity index (PDI) were derived using cumulant fit analysis. All measurements were conducted with automated attenuator adjustment and multiple scans (between 15-20) for accuracy. All data points represent the mean of three or more individually prepared samples.

TABLE 2

| Summary of DNA nanoparticle properties | | | | | | | |
|---|---|---|---|---|---|---|---|
| NP # | Material | Modified amines (%)[a] | N/P[f] | Hydrodynamic diameter (nm)[b] | Zeta potential (mV)[c] | Polydispersity index[b] | morphology[d] |
| 1 | N: PLL 0 | 0 | 3 | 90 ± 8 | 22 ± 1 | 0.34 ± 0.12 | sphere |
| 2 | N: PLL(M) 29 | 29 | 5 | 95 ± 10 | 19 ± 3 | 0.36 ± 0.11 | sphere |
| 3 | N: PLL(MN) 31 | 31 | 5 | 98 ± 8 | 20 ± 2 | 0.29 ± 0.08 | sphere |
| 4 | N: PLL(TM) 28 | 28 | 5 | 91 ± 6 | 16 ± 3 | 0.29 ± 0.08 | sphere |
| 5 | N: PEG-PLL 0 | 0 | 3 | 99 ± 8 | 1.7 ± 0.5 | 0.32 ± 0.09 | mixed[e] |
| 6 | N: PEG-PLL(M) 33 | 33 | 5 | 100 ± 8 | 2.9 ± 0.4 | 0.29 ± 0.09 | mixed[e] |
| 7 | N: PEG-PLL(MN) 31 | 31 | 5 | 106 ± 9 | 1.6 ± 0.7 | 0.34 ± 0.07 | mixed[e] |
| 8 | N: PEG-PLL(TM) 30 | 30 | 5 | 103 ± 8 | 2.2 ± 0.4 | 0.31 ± 0.07 | mixed[e] |

[a]Determined by $^{1}H$ NMR
[b]Determined by dynamic light scattering
[c]Determined by electrophoretic light scattering/lase doppler electrophoresis
[d]Determined by transmission electron microscopy
[e]Toriods and rods
[f]N/P = Molar amine to phosphate ratio Results Experiment 1 a) Buffering

Acid-base titrations of the polymer solutions were conducted to evaluate their buffering capacity/ability to maintain pH upon addition of acidic solution and intracellular lysosomal buffering studies were conducted to further assess the materials buffering capacity.

a) Acid-Base Titration

Polymer PEG (5K)-PLL (50 units) (Alamada Polymers), PEI (25K, Polysciences Inc), "P: PEG-PLL (M) 35" (Polymer 12), "P: PEG-PLL (MN) 39" (Polymer 15) and "P: PEG-PLL (TM) 33" (Polymer 18) solutions (3 mL) were prepared at 1 mg/mL in 150 mM NaCl and titrated to a pH of 11 by addition of 1 M NaOH. While stirring, polymer solutions were titrated to pH 4.5 with 0.1 M HCl at 5 μL increments. The buffering capacity was reported as the average volume (μL) needed to change the polymer solution pH by 0.5. The change in the protonation degree between extracellular neutral pH 7.4 and endosomal acidic pH 4.5 (Aa7.4-4.5) was calculated as the moles of HCl added to change the pH from 7.4 to 4.5 divided by the total moles of amine per solution. All titration experiments were performed in triplicate. The results are shown in FIG. 1A.

b) Lysosomal Buffering

Figure 1B:
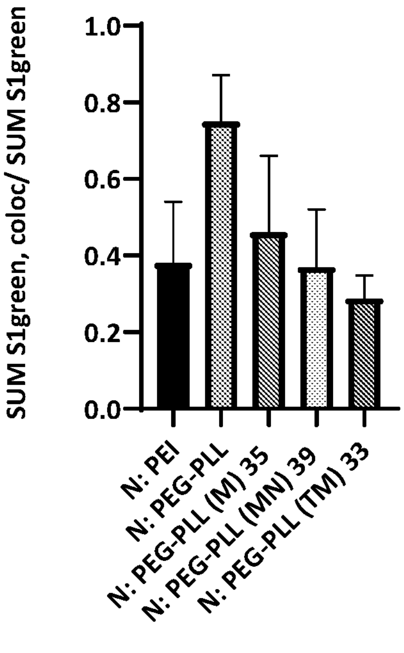
FIG. 1B: Shows the results from Buffering Experiment 1b): Lysosomal Buffering. The buffering properties of the identified polymers in live cells is presented as the Mander's Overlap Coefficient (0-1): neutral pH signal colocalized with acidic pH signal/overall green-neutral pH signal. Mander's coefficient is a measure from 0 to 1 that can roughly be defined as the ratio of complexes that acidified versus total complexes. If buffering happens, the cells remain associated with the neutral pH signal, if it does not, the cells become increasingly associated with the acidic pH signal.

Gwiz Luciferase (Genlantis, San Diego CA) was labelled with two fluorophores, a pH-insensitive green dye and a pH sensitive red dye to enable pH estimation by measuring the green:red fluorescence ratio colocalized in the same pixels. First, DNA was labelled using the MFP488 LabelIT® Nucelic Acid kit (Mirus Bio LLC, Madison WI) and then amine-functionalized with the Amine LabelIT® Nucelic Acid kit (Mirus Bio LLC, Madison WI) using the manufacturer's suggested protocol. Ethanol precipitation was used to removed non-reacted dye. The DNA was subsequently labelled with NHS ester pHRODO red (Thermo Fischer, Waltham, MA) and purified via ethanol precipitation. Spectrophotometry was used to confirm and quantify modification of the DNA with the different fluorophores (approximately 40 dyes per plasmid). MFP-488 and pHRODO red dual-labelled DNA was then used to prepare nanoparticles as described below. For cell studies, H1299 cells were seeded at 10,000 cells per well in 96-well plates and allowed to attach for 24 h in Roswell Park Memorial Institute (RPMI) media supplemented with 10% FBS and 1% P/S. Next, cells were washed twice with 100 μL of PBS and once with 100 μL of OPTI-MEM. DNA nanoparticles were prepared with PEI, PEG-PLL, "P: PEG-PLL (M) 35" (Polymer 12), "P: PEG-PLL (MN) 39" (Polymer (15) and "P: PEG-PLL (TM) 33" (Polymer 18)) by mixing DNA (66.6 μg/mL) and polymer solutions in 20 mM HEPES at an amine to phosphate ratio of 5 (final DNA concentration of 33.3 μg/mL) as described above. The NPs were then added to the cells at 0.1 μg of DNA per well in OPTI-MEM (1:10 dilution). After a 4-hour period, cells were treated with a Hoechst stain (5 μg/mL stock in PBS for 5 minutes) and imaged using fluorescent microscopy with the EVOS Cell Imaging System (Thermo Fischer, Waltham, MA). A scale bar approximating intracellular pH was generated by imaging fixed, permeabilized cells after nanoparticle treatment in buffers at acidic, neutral, and basic buffers. In this assay pHRODO red signal dramatically increases as pH decreases while MFP488 is pH insensitive, therefore acidic vesicles appear red or orange and neutral vesicles appear green. The results are shown in FIG. 1B.

Experiment 2

Nanoparticle Stability

Nanoparticle stability was assessed against anionic dissociation and in intravital pharma kinetic (PK) studies.

a) Anionic Dissociation

Figure 2A:
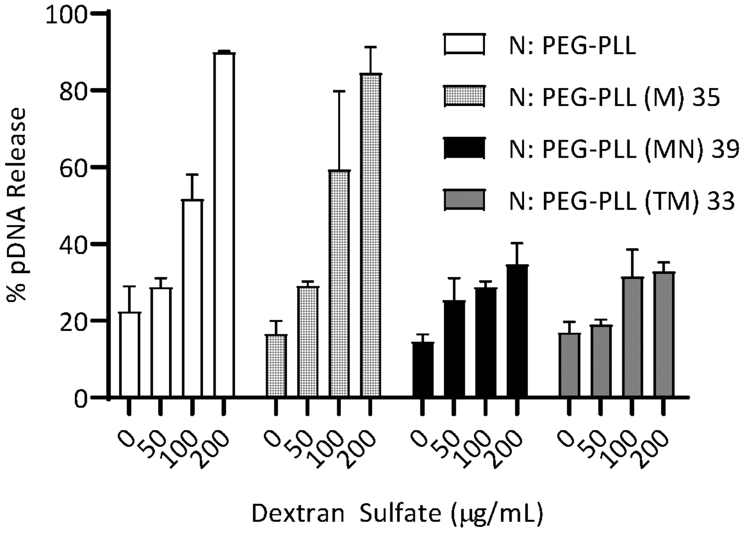
FIG. 2A. Shows the results from Nanoparticle Stability Experiment 2a) Anionic Dissociation. Stability assessment of nanoparticles towards anionic displacement of pDNA by dextran sulfate (DS) quantified by DNA band intensities of nanoparticles exposed to different concentrations of DS and analysed via gel electrophoresis.

Nanoparticles were prepared as described above in Example 5 with PEG-PLL and Polymers 12, 15 and 19 at an N:P of 5 with 2 μg of Gwiz Luciferase DNA (Genlantis, San Diego, CA). 20 mM HEPES buffer and dextran sulphate (DS) (Sigma-Aldrich, 5 g/mL in 20 mM HEPES buffer) solution was added to each nanoparticle sample so the final pDNA concentration remained constant and the DS concentration varied between 0 and 200 mg/mL. After a 30-minute treatment period at 3TC, 15 μL of each formulation was added to a 2% electrophoresis gel (Thermo Fischer Scientific) with ethidium bromide and run for 10 minutes using the standard E-gel protocol. The results are shown in FIG. 2A.

b) Nanoparticle Stability in the Bloodstream

Figure 2B:
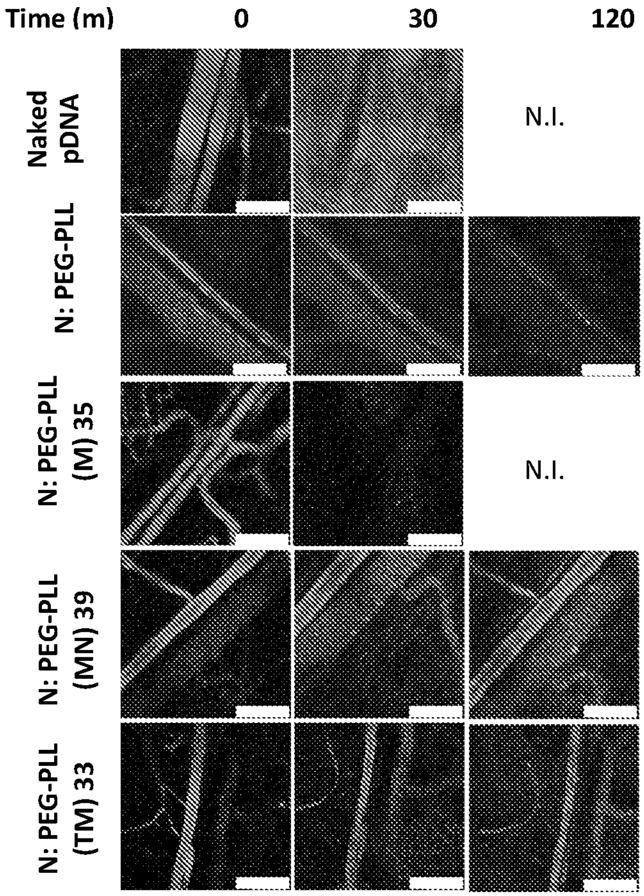
FIG. 2B. Shows the results from Nanoparticle Stability Experiment 2b) Nanoparticle stability in the bloodstream. Representative intravital ear-lobe PK images acquired at different time points post-tail vein injection of Cy5-pDNA nanoparticles where signal in the vascular structures indicated the NPs remain in circulation. Scalebars represent 100 μm.

Nanoparticle stability in the bloodstream was determined by multi-photon confocal fluorescence microscopy imaging of blood vessels in the earlobes of mice. Nanoparticles solutions were prepared as described in Example 5 with PEG-PLL and Polymers 12, 15 and 19 using Cy5-labeled pDNA (20 dyes/plasmid) at 100 μg of DNA/mL in 5% trehalose solution (N:P=5). Balb/c mice were subsequently anesthetized with isoflurane in an induction chamber before being transferred to a nose cone located on the microscope stage. The ear of the mouse was then positioned and flattened using a custom slide holder and glass slide to enable imaging with a Leica SP8 DIVE multi-photon microscope. A 25×1.0 NA water immersion objective with an M32 back aperture was used for the imaging of the nanoparticles. The Cy5 dye was excited using the 1220 nM line of a Spectra-Physics X3 laser. Two non-descanned detectors of the DIVE system were used for imaging. One DIVE HyD detector was tuned to 605-615 nM for second harmonics imaging. The second detector was tuned to 635-775 nM for Cy5 emission detection. Second harmonics was used to locate a field of view with a vein and artery, after which mice were I.V. administered the nanoparticle formulations through a tail vein injection of 200 μL (20 μg of pDNA). Mice were imaged until the signal within the vessels equated that in the surrounding tissue or for a 2-hour period. Image) was used to generate maximum intensity projections of images collected over a is period for each specified time point. Each formulation was tested in a minimum of 3 mice. The results are shown in FIG. 2B.

Experiment 3

Nanoparticle Transfections

Nanoparticle stability was assessed against anionic dissociation and in circulation.

Figure 3A:
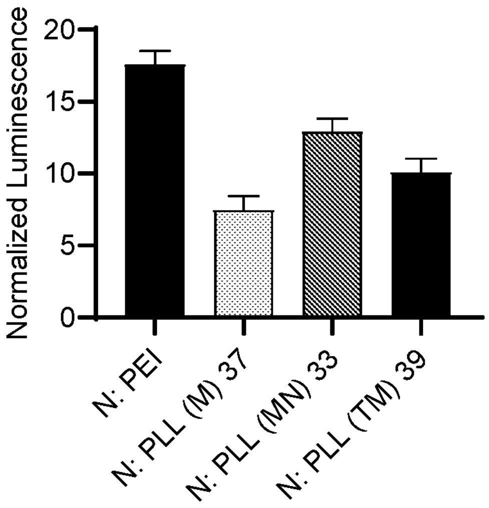
FIG. 3A. Shows the results from Nanoparticle Transfections Experiment 3). Transfection of H1299 cells. Normalized luminescence after cells were treated with poly-L-lysine (PLL) nanoparticles encoding luciferase in OPTI-MEM.
Figure 3B:
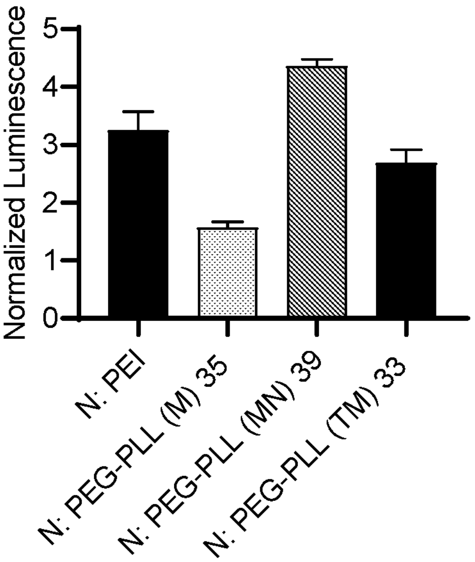
FIG. 3B. Shows the results from Nanoparticle Transfections Experiment 3). Transfection of H1299 cell in Serum. Normalized luminescence after cells were treated with PLL nanoparticles encoding luciferase in media supplemented with 10% FBS and 100 nM chloroquine.

H1299 and C2C12 cells were seeded in 96-well plates at 10,000 cells/well in RPMI media or 20,000 cells/well in Dulbecco's Modified Eagle Medium (DMEM) supplemented with 10% fetal bovine serum (FBS) and 1% penicillin streptomycin (P/S). Before transfection H1299 cells were allowed a recovery period of 241, while C2C12 myoblasts were differentiated into myotubes through incubation in DMEM supplemented with 2% horse serum for a minimum of 7 days. Subsequently, cells were washed twice with 100 μL of PBS and once with culture media or modified Eagle's Minimum Media (OPTI-MEM). Nanoparticles were prepared as described in Example 5 with PEI, PLL, "PLL (M) 37" (Polymer 2), "PLL (MN) 33" (Polymer 5), "PLL (TM) 39" (Polymer 8), PEG-PLL, "PEG-PLL (M) 35" (Polymer 12), "PEG-PLL (MN) 39" (Polymer 15), "PEG-PLL (TM) 33" (Polymer 18). Non-modified PEI, PLL and PEG-PLL nanoparticles were prepared with 1 μg of DNA at an N:P of 3 and the modified PLL nanoparticles at an N:P of 5. After complexation, NPs were added to the cells at 0.1 μg of DNA per well in either OPTI-MEM (1:10 dilution) or culture media. After a 16-hour period, the nanoparticle supplemented media was removed, and fresh culture media was added. Green fluorescent protein (GFP) expression was imaged using the Incucyte (Essen BioScience, Ann Arbor, MI) and luciferase/viability quantified using the standard protocol for the ONE-Glo™+ Tox Luciferase Reporter (Promega, Madison, WI) and PHERAstarFSX instrument (BMG Lab Tech, Cary, NC). The results are shown in FIGS. 3 and 4.

4) Toxicity

Material toxicity was assessed using live dead assays.

H1299 cells were seeded in 96-well plates (10000/well). After a 24 h recovery period, cells were treated with 0.1 to 2 μg of PEI (25K, Polyscience, Inc., Philadelphia PA), PLL (Alamanda Polymers, Inc., Huntsville AL, 5 kDa), and P: PLL(M) 33, P: PLL(MN) 33, and P: PLL(TM) 33" prepared in OPTI-MEM. After a 16-hour exposure, cells were analysed using a live/dead stain or metabolic assay. For the live/dead assay, 10 μL of Calcein AM (2 mM in DMSO) and 5 of propidium iodide (2 mM DMSO) stock solutions were dissolved in 5 mL of PBS. The cells were then washed with PBS twice and staining solution added (100 μL/well). After a 30-minute incubation period at 37° C., the cells were imaged using an IncuCyte plate reader (Sartorius). Alternatively, metabolic assays were performed using Celriter-Glo·Luminescent Assay using the manufacturers standard protocol. Luminescence measurements were collected using a PHERAStar plate reader (BMG LabTech) and $IC_{50}$ doses were derived by fitting the data in Microsoft excel.

TABLE 3

Toxicity/$IC_{50}$ (μg/well) of polymer materials in vitro
a Cell line tested

| material | H1299[a] | C2C12[a] |
|---|---|---|
| P: PEI | 0.43 | 0.82 |
| P: PLL | 0.21 | 0.33 |
| P: PLL(M) 33 | 0.40 | 0.41 |
| P: PLL(MN) 33 | 0.45 | 0.90 |
| P: PLL(TM) 33 | 1.78 | 1.89 |

5) Intramuscular Transfection

Nanoparticle transfection efficiency was assessed in vivo through monitoring the expression of reporter protein luciferase after intramuscular injection.

Figure 5:
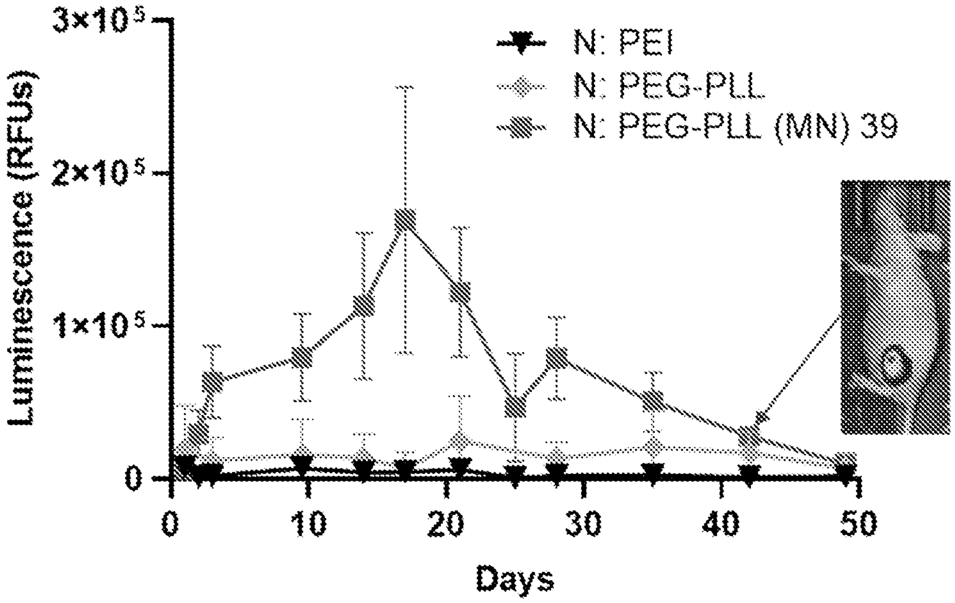
FIG. 5 Shows the results from Intramuscular Transfection Experiment 5). Mouse Intramuscular Luciferase Expression. Luminescence in mouse hind limbs post intramuscular injection with 5 μg of complexed pDNA assessed via IVIS and IVIS Perkin Elmer software (n=8).

Nude (nu/nu) mice were intramuscularly injected with 5 μg of DNA complexed with PEI, PEG-PLL or P: PEG-PLL (MN) 39 (Polymer (15)) in 50 μL of 5% trehalose solution per hind limb (n=2 per mouse). Expression was assessed daily/weekly using IVIS (Perkin Elmer) whereupon mice were administered 150 μL of Rediiect (30 mg/mL Luciferin-D) with an IP injection. Luminescence was collected in quadruplicate and presented as the mean+/−standard deviation. The results are shown in FIG. 5.

What is claimed is:

1. A modified lysine selected from:

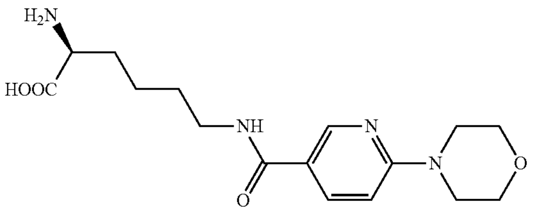 [SMILES: N[C@@H](CCCCNC(=O)c1ccc(N2CCOCC2)nc1)C(=O)O]

(2S)-2-amino-6-{[6-(morpholin-4-yl)pyridine-3-carbonyl]amino}hexanoic acid;

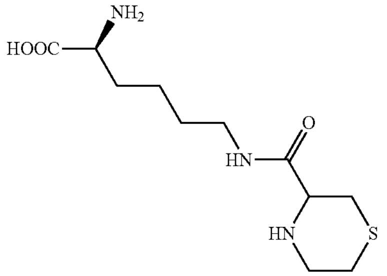 [SMILES: N[C@@H](CCCCNC(=O)C1CSCCN1)C(=O)O]

(2S)-2-amino-6-[(thiomorpholine-3-carbonyl)amino] hexanoic acid; and

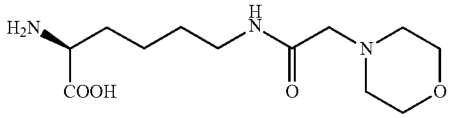 [SMILES: N[C@@H](CCCCNC(=O)CN1CCOCC1)C(=O)O]

(2S)-2-amino-6-[2-(morpholin-4-yl) acetamido]hexanoic acid, or a pharmaceutically acceptable salt thereof.

2. A polypeptide comprising one or more modified lysine residues of claim 1.

3. The polypeptide of claim 2 wherein fewer than 50% of the amino acid residues are modified lysine residues and the remainder are unmodified lysine residues.

4. The polypeptide of claim 2 further comprising a polyethylene glycol polymer.

5. A pharmaceutical composition which comprises the polypeptide of claim 2 and a pharmaceutically active agent.

6. The pharmaceutical composition of claim 5 wherein the pharmaceutically active agent is genetic material.

7. The pharmaceutical composition of claim 6 wherein the genetic material is DNA.

8. A method of gene therapy in a warm-blooded animal, which comprises administering to said animal an effective amount of a pharmaceutical composition of claim 5.

* * * * *